United States Patent [19]

Glock et al.

[11] Patent Number: 5,541,148
[45] Date of Patent: Jul. 30, 1996

[54] SELECTIVE SAFENED HERBICIDAL COMPOSITION COMPRISING 2-ETHOXYCARBONYL-3-(4,6-DIMETHOXY-PYRIMIDINE-2-YL) OXY-PYRIDINE AND AN ACYLSULFAMOYLPHENYL-UREA SAFENER

[75] Inventors: Jutta Glock, Mumpf, Switzerland; Elmar Kerber, Görwihl, Germany

[73] Assignee: Ciba-Geigy Corporation, Tarrytown, N.Y.

[21] Appl. No.: 343,397

[22] Filed: Nov. 22, 1994

Related U.S. Application Data

[63] Continuation-in-part of Ser. No. 85,334, Jun. 30, 1993, abandoned.

[30] Foreign Application Priority Data

| Jul. 8, 1992 | [CH] | Switzerland | 2148/92 |
| Sep. 25, 1992 | [CH] | Switzerland | 3007/92 |
| Feb. 11, 1993 | [CH] | Switzerland | 423/93 |

[51] Int. Cl.⁶ ............................................. A01N 25/32
[52] U.S. Cl. .................................................... 504/112
[58] Field of Search ....................................... 504/112

[56] References Cited

U.S. PATENT DOCUMENTS

| 3,959,304 | 5/1976 | Teach | 260/307 FA |
| 4,256,481 | 3/1981 | Gardi et al. | 71/88 |
| 4,448,960 | 5/1984 | Rohr | 544/282 |
| 4,493,726 | 1/1985 | Burdeska et al. | 71/87 |
| 4,530,716 | 7/1985 | Martin et al. | 71/88 |
| 4,601,745 | 7/1986 | Moser | 71/88 |
| 4,639,266 | 1/1987 | Heubach et al. | 71/92 |
| 4,902,340 | 2/1990 | Hubele | 71/94 |
| 4,929,720 | 5/1990 | Hansen | 534/766 |
| 4,971,618 | 11/1990 | Pallos et al. | 71/93 |
| 5,078,780 | 1/1992 | Moser et al. | 71/92 |
| 5,085,686 | 2/1992 | Vogelbacker et al. | 71/92 |
| 5,167,693 | 12/1992 | Drewes et al. | 71/92 |
| 5,215,570 | 6/1993 | Burckhardt et al. | 504/104 |

FOREIGN PATENT DOCUMENTS

| 0055693 | 7/1982 | European Pat. Off. . |
| 0089313 | 9/1983 | European Pat. Off. . |
| 0094349 | 11/1983 | European Pat. Off. . |
| 0149974 | 7/1985 | European Pat. Off. . |
| 0174562 | 3/1986 | European Pat. Off. . |
| 0249707 | 12/1987 | European Pat. Off. . |
| 0268554 | 5/1988 | European Pat. Off. . |
| 0304409 | 2/1989 | European Pat. Off. . |
| 0315898 | 5/1989 | European Pat. Off. . |
| 0335409 | 10/1989 | European Pat. Off. . |
| 0347811 | 12/1989 | European Pat. Off. . |
| 0365484 | 4/1990 | European Pat. Off. . |
| 0374839 | 6/1990 | European Pat. Off. . |
| 0402751 | 12/1990 | European Pat. Off. . |
| 0409369A2 | 1/1991 | European Pat. Off. . |
| 0426476A1 | 5/1991 | European Pat. Off. . |
| 0435170A2 | 7/1991 | European Pat. Off. . |
| 0436484 | 7/1991 | European Pat. Off. . |
| 0459243A2 | 12/1991 | European Pat. Off. . |
| 0492367 | 7/1992 | European Pat. Off. . |
| 0521407 | 1/1993 | European Pat. Off. . |
| 0547546 | 6/1993 | European Pat. Off. . |
| 2948535 | 6/1981 | Germany . |
| 4123469 | 1/1993 | Germany . |
| WO91/05781 | 5/1991 | WIPO . |
| WO92/17468 | 10/1992 | WIPO . |
| WO93/00010 | 1/1993 | WIPO . |

OTHER PUBLICATIONS

CA 115:71629r (1991).
Chemical Abstract, 117, 126460c (1992).
Chemical Abstract, 118, 228253a, (1993).
5–Igrochemical, 119, 133472C (1993).Brighton Crop Protection Conference–Weeds–1993, K. Kreuz.
C. Tomlin–The Pesticide Manual, 10th edition, pp. 84, 85, 214, 226, 227, 305, 306, 378, 379, 431, 432, 433, 499, 500, 517 & 537. 1994.

*Primary Examiner*—S. Mark Clardy
*Attorney, Agent, or Firm*—Edward M. Roberts

[57] ABSTRACT

A selective herbicidal composition for the control of grasses and weeds in crops of useful plants comprises a) a herbicidally effective amount of a pyrimidine of formula I

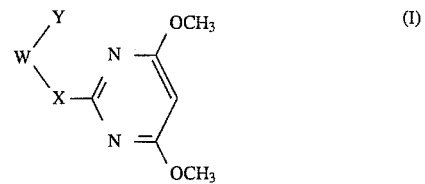

wherein the substituents are defined in claim 1 and b) as safener a herbicide-antagonistically effective amount of an N-acylsulfamoylphenylurea of formula IIb

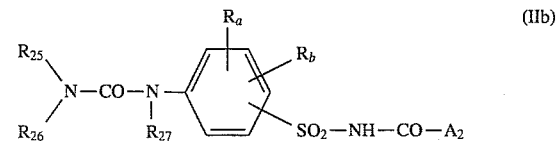

wherein the substituents are defined in claim 1.

4 Claims, No Drawings

SELECTIVE SAFENED HERBICIDAL COMPOSITION COMPRISING 2-ETHOXYCARBONYL-3-(4,6-DIMETHOXY-PYRIMIDINE-2-YL) OXY-PYRIDINE AND AN ACYLSULFAMOYLPHENYL-UREA SAFENER

This is a continuation-in-part of application Ser. No. 08/085,334 of Jun. 30, 1993, now abandoned.

The present invention relates to a selective herbicidal composition for controlling grasses and weeds in crops of useful plants, especially in cereal crops, which comprises a herbicide and a safener (antidote) which protects the useful plants, but not the weeds, from the phytotoxic action of the herbicide, and to the use of that composition or of the combination of herbicide and safener in the control of weeds in crops of useful plants.

When herbicides are used, considerable damage may be caused to the crop plants depending on such factors as the concentration of herbicide and the mode of application, the species of crop plant, the nature of the soil and climatic conditions, for example period of exposure to light, temperature and rainfall. In particular, severe damage can be caused if, in the course of crop rotation, crop plants that are resistant to the herbicides are followed by other crop plants that have no or only insufficient resistance towards the herbicides.

In order to counter that problem, various compounds have already been proposed that are capable of specifically antagonising the damaging effect of the herbicide on the crop plant, that is to say of protecting the crop plant without at the same time significantly affecting the herbicidal action against the weeds to be controlled. It has been found that the proposed safeners are often very species- or type-specific both as regards the crop plants and as regards the herbicide and in some cases also as a function of the mode of application, that is to say a specific safener is often suitable only for a specific crop plant and a specific class of herbicidal compound.

For example, EP-A-0 094 349 discloses quinoline derivatives that protect crop plants from the phytotoxic action of herbicides of specific classes of compounds, such as phenoxypropionic acid ester herbicides, ureas, carbamates or diphenyl ethers.

It has now been found that very specific safeners selected from the classes of the N-acylsulfamoylphenylureas, quinoline derivatives, chloroacetamides and 1-phenylazole- 3-carboxylic acid derivatives are suitable for protecting crop plants from the phytotoxic action of a specific class of pyrimidine herbicides.

There is therefore proposed according to the invention a selective herbicidal composition that comprises as active component, in addition to inert additives such as carriers, solvents and wetting agents, a mixture comprising a) a herbicidally effective amount of a pyrimidine of formula I

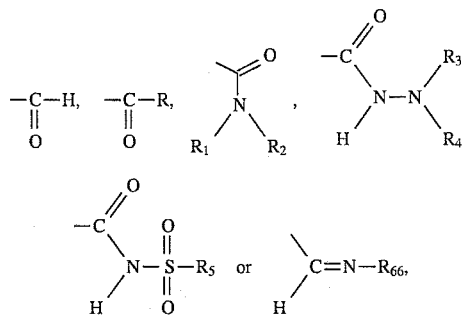

wherein

X is oxygen or sulfur or, when W is $W_5$, may also be NH, NC(O)H or NC(O)$R_{62}$;

Y is —COOH, or an organic or inorganic salt of that acid,

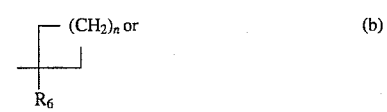

or the possible salts of these groups;

R is —OR$_{11}$;

R$_1$ is one of the groups (a), (b) and (c)

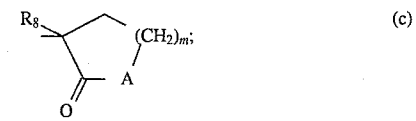

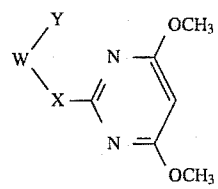

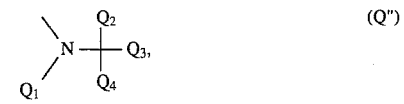

R$_2$ is hydrogen, methyl or the group Q"

$$\begin{matrix} \diagdown & Q_2 \\ N & Q_3, \\ \diagup & Q_4 \\ Q_1 \end{matrix} \quad (Q'')$$

wherein

Q$_1$ is hydrogen, methyl or, together with Q$_4$, is —(CH$_2$)$_2$—, —(CH$_2$)$_3$—, —CH$_2$CH(OH)CH$_2$— or —CH$_2$SCH$_2$—;

Q$_2$ is hydrogen or methyl;

Q$_3$ is hydrogen, trifluoromethyl, ethynyl, vinyl, phenyl, cyano or C$_{1-4}$-alkoxycarbonyl, C$_{1-4}$alkyl, or C$_{1-4}$alkyl substituted by hydroxy, C$_{1-4}$alkoxy, mercapto, C$_{1-4}$alkylmercapto, vinyl, phenyl, 4-hydroxyphenyl, 4-imidazolyl, 3-indolyl, hydroxycarbonyl, C$_{1-4}$alkoxycarbonyl, 2-propenyloxycarbonyl, cyano or by carbamoyl; and Q$_4$ is hydrogen, methyl, hydroxymethyl, formyl or cyano;

or R$_2$ together with R$_7$ is —(CH$_2$)$_p$—, —CH$_2$SCH$_2$— or —CH$_2$CHOHCH$_2$—;

R$_3$ is hydrogen, C$_{1-4}$alkyl, phenyl, or phenyl mono- or di-substituted by fluorine, chlorine, bromine, methyl, trifluoromethyl, methoxy or by nitro;

R$_4$ is hydrogen or methyl;

R$_5$ is C$_{1-6}$alkyl, C$_{1-6}$haloalkyl, phenyl, benzyl, or phenyl substituted by fluorine, chlorine, bromine, methyl, trifluoromethyl, methoxy, nitro, cyano, carboxy or by C$_{1-3}$alkoxycarbonyl;

R$_6$ is hydrogen, hydroxymethyl, formyl, cyano, hydroxyimino, C$_{1-4}$alkoxyimino, phosphono, phosphino, methylphosphino or a group COX$_1$;

R$_7$ is hydrogen; C$_{1-4}$alkyl or C$_{1-4}$alkyl substituted by hydroxy, C$_{1-4}$alkoxy, mercapto, acylmercapto, C$_{1-4}$alkylthio, vinyl, phenyl, 4-hydroxyphenyl, 4-imidazolyl, 3-indolyl, hydroxycarbonyl, C$_{1-4}$alkoxycarbonyl, 2-propenyloxycarbonyl, cyano, carbamoyl, methylphosphino or by methylsulfoximino; trifluoromethyl; ethynyl; vinyl or vinyl substituted by chlorine or by methoxy; phenyl or phenyl substituted by fluorine, chlorine, methyl, trifluoromethyl or by methoxy; or cyano or $C_{1-4}$alkoxycarbonyl;

$R_8$ is hydrogen or methyl;

A is oxygen, sulfur or —NH—;

m is 1, 2 or 3;

n is 0, 1, 2 or 3;

p is 2 or 3;

$X_1$ is hydroxy, $C_{1-4}$alkoxy, $C_{3-4}$alkenyloxy, mercapto, $C_{1-4}$alkylthio, amino, $C_{1-4}$alkylamino, $C_{2-4}$dialkylamino or $C_{1-4}$alkoxyamino; or $C_{1-4}$alkoxy, $C_{3-4}$alkenyloxy, mercapto, $C_{1-4}$alkylthio, amino, $C_{1-4}$alkylamino, $C_{2-4}$dialkylamino or $C_{1-4}$alkoxyamino each substituted by phenyl, benzyloxy or by $C_{1-2}$alkoxy, or is one of the groups (d), (e) and (f)

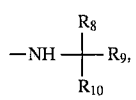 (d)

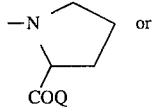 (e)

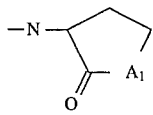 (f)

wherein $A_1$ is oxygen, sulfur or —NH—;

$R_9$ is hydrogen, $C_{1-4}$alkyl or benzyl;

$R_{10}$ is hydroxymethyl, cyano or a group COQ';

Q is hydroxy, $C_1$–$C_4$alkoxy, 2-propenyloxy, benzyloxy, amino or the group (d); and Q' is hydroxy, $C_1$–$C_4$alkoxy, 2-propenyloxy, benzyloxy, amino or the group (d);

$R_{11}$ is hydrogen, $C_1$–$C_{10}$alkyl, $C_1$–$C_4$alkoxy-$C_1$–$C_4$alkyl, $C_1$–$C_4$alkylthio-$C_1$–$C_4$alkyl, di-$C_1$–$C_4$alkylamino-$C_1$–$C_4$alkyl, halo-$C_1$–$C_8$alkyl, $C_2$–$C_8$alkenyl, halo-$C_2$–$C_8$alkenyl, $C_3$–$C_8$alkynyl, $C_3$–$C_7$cycloalkyl, halo-$C_3$–$C_7$cycloalkyl, $C_1$–$C_8$alkylcarbonyl, $C_1$–$C_4$alkylcarbonyloxy-$C_1$–$C_2$alkyl, allylcarbonyl, $C_3$–$C_7$cycloalkylcarbonyl, benzoyl that is unsubstituted or substituted at the phenyl ring by up to three identical or different substitents selected from halogen, $C_1$–$C_4$alkyl, halo-$C_1$–$C_4$alkyl, halo-$C_1$–$C_4$alkoxy and $C_1$–$C_4$alkoxy; or is furoyl or thienyl; or $C_1$–$C_4$alkyl substituted by phenyl, halophenyl, $C_1$–$C_4$alkylphenyl, $C_1$–$C_4$alkoxyphenyl, halo-$C_1$–$C_4$-alkylphenyl, halo-$C_1$–$C_4$alkoxyphenyl, $C_1$–$C_6$alkoxycarbonyl, $C_1$–$C_4$alkoxy-$C_1$–$C_8$alkoxycarbonyl, $C_3$–$C_8$alkenyloxycarbonyl, $C_3$–$C_8$alkynyloxycarbonyl, $C_1$–$C_8$alkylthiocarbonyl, $C_3$–$C_8$alkenylthiocarbonyl, $C_3$–$C_8$alkynylthiocarbonyl, carbamoyl, mono-$C_1$–$C_4$alkylaminocarbonyl, di-$C_1C_4$alkylaminocarbonyl, tri-$C_1C_6$alkylsilyl or by di-$C_1C_6$alkyl-phenylsilyl; or phenylaminocarbonyl that is unsubstituted or substituted at the phenyl by up to three identical or different substituents selected from halogen, $C_1C_4$alkyl, halo-$C_1$–$C_4$alkyl, halo-$C_1$–$C_4$alkoxy and $C_1$–$C_4$alkoxy or is monosubstituted by cyano or by nitro; or dioxolan-2-yl that is unsubstituted or substituted by one or two $C_1$–$C_4$alkyl radicals; oxetan-3-yl or dioxan-2-yl that are unsubstituted or substituted by one or two $C_1$–$C_4$alkyl radicals; or $C_1$–$C_4$alkyl substituted by cyano, nitro, carboxy or by $C_1$–$C_8$alkylthio-$C_1$–$C_8$alkoxycarbonyl; or the groups —N=C(CH$_3$)$_2$ or —CH$_2$CH$_2$ON=C(CH$_3$)$_2$;

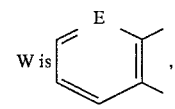 (W$_1$)

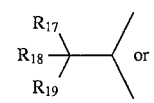 (W$_2$)

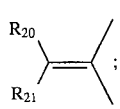 (W$_3$)

or W and Y together form a group W$_4$

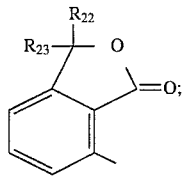 (W$_4$)

or W and Y together form a group W$_5$

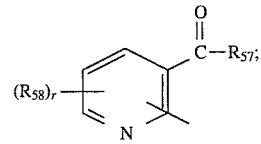 (W$_5$)

or W and Y together form a group W$_6$

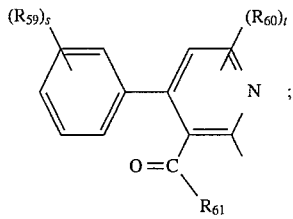 (W$_6$)

E is nitrogen or —CR$_{12}$;

$R_{12}$ is hydrogen, halogen, hydroxy, $C_1$–$C_4$alkoxy, phenyl or benzyl; or phenyl substituted by $C_1$–$C_4$alkyl, $C_1$–$C_4$alkoxy, $C_1$–$C_4$haloalkyl or by halogen; benzyl-substituted by $C_1$–$C_4$alkyl, $C_1$–$C_4$alkoxy, $C_1$–$C_4$haloalkyl or by halogen; —COR$_{13}$,

—S(O)$_q$R$_{16}$, (4,6-dimethoxy-pyrimidin- 2-yl)-oxy; $C_1$–$C_4$alkyl that is unsubstituted or substituted by halogen; ethenyl that is unsubstituted or substituted by $C_1$–$C_4$alkyl, phenyl, halogen, cyano or $C_1$–$C_4$alkoxycarbonyl; ethynyl that is unsubstituted or substituted by halogen, $C_1$–$C_4$alkyl or phenyl; phenoxy or phenylthio that are unsubstituted or substituted by $C_1$–$C_4$alkyl, $C_1$–$C_4$alkoxy, $C_1$–$C_4$haloalkyl or halogen;

$R_{13}$ is $C_1$–$C_4$alkyl, halo-$C_1$–$C_4$alkyl, $C_1$–$C_4$alkoxy-$C_1$–$C_4$alkyl; amino, $C_1$–$C_4$alkylamino, di-$C_1$–$C_4$alkylamino, $C_2$–$C_4$haloalkylamino, di-$C_2$–$C_4$haloalkylamino, $C_1$–$C_4$alkoxyalkylamino, di-$C_1$–$C_4$alkoxyalkylamino, $C_3$–$C_4$alkenylamino, diallylamino, -N-pyrrolidino, -N-piperidino, -N-morpholino, -N-thiomorpholino, -N-piperidazino, —O—N=C(CH$_3$)—CH$_3$ or —O—CH$_2$—CH$_2$—O—N=C(CH$_3$)—CH$_3$;

$R_{14}$ is hydrogen, $C_1$–$C_{10}$-alkyl that is unsubstituted or substituted by acyl or by cyano; $C_1$–$C_4$alkoxy-$C_1$–$C_4$alkyl, $C_1$–$C_4$alkylthio-$C_1$–$C_4$alkyl, $C_1$–$C_4$alkylsulfonyl-$C_1$–$C_4$alkyl, $C_1$–$C_4$alkylsulfinyl-$C_1$–$C_4$alkyl, or phenyl that is unsubstituted or substituted at the phenyl ring by up to three identical or different substituents selected from halogen, $C_1$–$C_4$alkyl, halo-$C_1$–$C_4$alkyl, halo-$C_1$–$C_4$alkoxy and $C_1$–$C_4$alkoxy;

$R_{15}$ is hydroxy, $C_1$–$C_{10}$alkyl that is unsubstituted or substituted by halogen; $C_1$–$C_6$alkoxy that is unsubstituted or substituted by halogen, benzyloxy, $C_1$–$C_6$alkoxycarbonyl, $C_3$–$C_6$cycloalkyl, acyl, di-$C_1$–$C_4$alkylamino or by $C_1$–$C_6$alkoxy; phenyl, phenoxy or benzyloxy each of which is unsubstituted or substituted at the phenyl ring by up to three identical or different substituents selected from halogen, $C_1$–$C_4$alkyl, halo-$C_1$–$C_4$alkyl, halo-$C_1$–$C_4$alkoxy and $C_1$–$C_4$alkoxy; $C_2$–$C_8$alkenyl, halo-$C_2$–$C_8$alkenyl, $C_3$–$C_8$alkynyl, $C_3$–$C_7$cycloalkyl, halo-$C_3$–$C_7$cycloalkyl, $C_1$–$C_4$alkoxyamino, $C_1$–$C_4$alkylamino, phenylamino, —OSi(CH$_3$)$_3$, $C_2$–$C_8$alkenyloxy or $C_3$–$C_8$alkynyloxy;

q is the number 0, 1 or 2;

$R_{16}$ is $C_1$–$C_{10}$alkyl that is unsubstituted or substituted by halogen; phenyl that is unsubstituted or substituted by up to three identical or different substituents selected from halogen, $C_1$–$C_4$alkyl, halo-$C_1$–$C_4$alkyl, halo-$C_1$–$C_4$alkoxy and $C_1$–$C_4$alkoxy; $C_2$–$C_8$alkenyl, halo-$C_2$–$C_8$alkenyl, $C_3$–$C_8$alkynyl, $C_3$–$C_7$cycloalkyl or halo-C$_3$–$C_7$cycloalkyl;

$R_{17}$ is hydrogen, $C_{1-6}$alkyl, $C_{3-6}$cycloalkyl, $C_{1-6}$alkyl that is monosubstituted by chlorine or mono- to hexa-substituted by fluorine; phenyl or thienyl, or phenyl mono- or disubstituted by fluorine, chlorine, methyl or by methoxy;

$R_{18}$ is hydrogen, methyl or, together with $R_{17}$, is —(CH$_2$)$_2$—, —(CH$_2$)$_3$—, —(CH$_2$)$_4$— or —(CH$_2$)$_5$—;

$R_{19}$ is hydrogen, methyl, fluorine, chlorine, bromine, $C_{1-6}$alkoxy, $C_{3-6}$alkenyloxy, $C_{3-6}$alkynyloxy, $C_{3-4}$cycloalkyl-$C_{1-2}$alkoxy, $C_{4-6}$cycloalkoxy, or $C_{1-4}$alkoxy that is monosubstituted by cyano, $C_{1-2}$alkoxy or by chlorine or mono- to hexa-substituted by fluorine; $C_{1-6}$alkylthio or cyano;

$R_{20}$ is hydrogen, $C_{1-4}$alkyl, $C_{1-3}$alkylthio or, together with $R_{21}$, is —(CH$_2$)$_4$—, —(CH$_2$)$_5$—, —S(CH$_2$)$_2$S— or —S(CH$_2$)$_3$S—;

$R_{21}$ is $C_{1-6}$alkyl, $C_{2-6}$alkenyl, $C_{3-6}$cycloalkyl, $C_{3-6}$haloalkalkyl, $C_{1-3}$alkoxy, $C_{1-3}$alkylthio, formyl, $C_{1-5}$alkylcarbonyl, carboxy, $C_{1-4}$alkoxycarbonyl, phenyl, or phenyl substituted by fluorine, chlorine, methyl, trifluoromethyl, methoxy or by nitro, or is 2-, 3- or 4-pyridyl, 2- or 3-furyl or 2- or 3-thienyl;

$R_{22}$ is hydrogen, $C_1$–$C_6$alkyl, $C_3$–$C_6$cycloalkyl, $C_1$–$C_6$haloalkyl, $C_3$–$C_6$alkenyl, $C_3$–$C_6$alkynyl, $C_3$–$C_6$haloalkenyl, $C_3$–$C_6$haloalkynyl, phenyl or benzyl, or phenyl substituted by $C_1$–$C_4$alkyl, $C_1$–$C_4$alkoxy, $C_1$–$C_4$haloalkyl or by halogen; benzyl substituted by $C_1$–$C_4$alkyl, $C_1$–$C_4$alkoxy, $C_1$–$C_4$haloalkyl or by halogen; halogen, hydroxy, —CHO, —COOH, phenoxy, cyano, phenylthio, —CONH$_2$, —OCHO, $C_2$–$C_5$alkanoyloxy, $C_2$–$C_5$alkoxycarbonyloxy, $C_2$–$C_3$alkylcarbamoyloxy, di($C_1$–$C_2$alkyl)carbamoyloxy or di($C_1$–$C_2$alkoxy)phosphonyl;

$R_{23}$ is hydrogen, $C_1$–$C_6$alkyl or CF$_3$;

r is 0, 1, 2 or 3;

s is 0, 1, 2 or 3;

m is 0, 1 or 2;

$R_{57}$ is hydrogen, hydroxy, $C_1$–$C_6$alkoxy, $C_1$–$C_6$alkoxyalkoxy, $C_1$–$C_6$acyloxyalkoxy, trimethylsilylethoxy, $C_1$–$C_6$alkylsulfonylamino, $C_1$–$C_6$alkylthio, imidazolyl, benzyloxy, phenoxy or thiophenoxy, or benzyloxy, phenoxy or thiophenoxy;

$R_{58}$ is halogen, $C_1$–$C_6$haloalkyl, $C_1$–$C_6$alkyl, acylamino, $C_3$–$C_6$cycloalkyl, halosubstituted $C_3$–$C_6$cycloalkyl, $C_2$–$C_6$alkenyloxy, $C_3$–$C_6$alkynyloxy, $C_1$–$C_6$alkoxycarbonyl, $C_1$–$C_6$alkoxy, $C_1$–$C_6$alkylamino, di-$C_1$–$C_6$alkylamino, $C_1$–$C_6$alkoxyiminoalkyl, acyl, $C_1$–$C_6$alkylthio, phenyl, benzyl, phenylamino or benzylamino;

$R_{59}$ is halogen, $C_1$–$C_6$alkyl, $C_1$–$C_6$alkoxy, $C_1$–$C_6$alkylamino, di-$C_1$–$C_6$alkylamino, $C_1$–$C_6$haloalkyl, $C_1$–$C_6$haloalkoxy, nitro, hydroxy, cyano, $C_1$–$C_6$alkoxyalkoxy, $C_1$–$C_6$alkoxycarbonylalkoxy, $C_1$–$C_6$alkylthioalkoxy, $C_1$–$C_6$alkylthio, $C_1$–$C_6$alkoxyalkyl, $C_2$–$C_6$alkenyl, $C_3$–$C_6$alkynyl, benzyloxy or phenoxy;

$R_{60}$ is halogen, $C_1$–$C_6$alkyl, $C_1$–$C_6$haloalkyl, $C_3$–$C_6$cycloalkyl, halo-substituted $C_3$–$C_6$cycloalkyl, $C_1$–$C_6$alkenyloxy, $C_3$–$C_6$alkynyloxy, $C_1$–$C_6$alkoxycarbonyl, $C_1$–$C_6$alkoxy, $C_1$–$C_6$alkylamino, di-$C_1$–$C_6$alkylamino, phenyl, benzyl, $C_1$–$C_6$alkoxyiminoalkyl, acyl, $C_1$–$C_6$alkylthio, phenylamino or benzylamino;

$R_{61}$ is hydrogen, hydroxy, $C_1$–$C_6$alkoxy, $C_1$–$C_6$alkoxyalkoxy, $C_1$–$C_6$acyloxyalkoxy, trimethylsilylethoxy, $C_1$–$C_6$alkylsulfonylamino, $C_1$–$C_6$alkylthio, imidazolyl, benzyloxy, phenoxy or thiophenoxy, or benzyloxy, phenoxy or thiophenoxy;

$R_{62}$ is $C_1$–$C_6$alkyl or $C_1$–$C_6$alkoxy;

$R_{66}$ is $C_1$–$C_6$alkyl, or $C_1$–$C_6$alkyl which is substituted by up to 3 fluorine atoms, 1 chlorine atom, 1 $C_{1-4}$alkoxy group, 1 $C_{1-4}$alkoxycarbonyl group, 1 dimethylcarbamoyl group, 1 carbamoyl group, 1 cyano group, 1 vinyl group, 1 ethynyl group or 1 phenyl group which is unsubstituted by fluorine, chlorine, bromine, methyl, trifluoromethyl or methoxy, or is phenyl, or phenyl which is up to trisubstituted by fluorine, chlorine, bromine, methyl, trifluoromethyl, methoxy or nitro; or NR$_{67}$R$_{68}$; or OR$_{69}$;

$R_{67}$ is hydrogen or $C_1$–$C_4$alkyl;

$R_{68}$ is hydrogen, $C_1$–$C_6$alkyl, phenyl, pyridyl, or phenyl which is monosubstituted to trisubstituted or pyridyl which is monosubstituted by $C_1$–$C_4$alkyl, fluorine, chlorine, bromine, trifluoromethyl, methoxy or nitro; or is $C_1$–$C_6$alkylcarbonyl, trifluoromethylcarbonyl, $C_3$–$C_6$cycloalkylcarbonyl, benzylcarbonyl, 2-, 3- or 4-pyridylcarbonyl, 2- or 3-furyl- or thiophenylcarbonyl, benzoyl, or benzoyl which is monosubstituted to disubstituted by fluorine, chlorine, bromine, methyl, trifluoromethyl, methoxy or nitro; or $C_1$–$C_4$alkoxycarbonyl, benzoyloxycarbonyl, aminocarbonyl, aminothiocarbonyl, or aminocarbonyl or aminothiocarbonyl each of which is monosubstituted to disubstituted by phenyl or $C_1$–$C_4$alkyl, it being possible for the phenyl group to be substituted by fluorine, chlorine, methyl or methoxy; and $R_{69}$ is hydrogen, $C_1$–$C_6$alkyl or $C_2$–$C_6$alkenyl, or $C_2$–$C_6$alkenyl which is substituted by halogen or phenyl, or $C_1$–$C_4$alkoxycarbonyl-$C_1$–$C_4$alkyl or $C_1$–$C_4$alkylthiocarbonyl-$C_1$–$C_4$alkyl;

and b) as safener, a herbicide-antagonistically effective amount of a quinoline derivative of formula IIa $$\text{(IIa)}$$

[Structure: quinoline with X₂ substituent and O—CH₂—C(=O)—O—R₂₄ group]

wherein $R_{24}$ is hydrogen or $C_1$–$C_8$alkyl and
$X_2$ is hydrogen or chlorine;

or of an N-acylsulfamoylphenylurea of formula IIb $$\text{(IIb)}$$

[Structure: $R_{25}$, $R_{26}$ on N—CO—N($R_{27}$)—phenyl(with $R_a$, $R_b$)—SO₂—NH—CO—A₂]

wherein
$A_2$ is a group

[Structures shown: phenyl with $R_g$, $R_h$, $R_c$; pyridine with $R_d$, $R_e$, $R_f$; naphthyl with $R_d$, $R_e$, $R_f$; furan with $R_d$, $R_e$; thiophene with $R_d$, $R_e$]

$R_{25}$ and $R_{26}$, independently of one another, are hydrogen, $C_1$–$C_8$alkyl, $C_3$–$C_8$cycloalkyl, $C_3$–$C_6$alkenyl, $C_3$–$C_6$alkynyl,

[phenyl ring with $R_x$, $R_y$]

or $C_1$–$C_4$alkyl substituted by $C_1$–$C_4$alkoxy or by

[phenyl ring with $R_x$, $R_y$];

or $R_1$ and $R_2$ together form a $C_4$–$C_6$alkylene bridge that can be interrupted by oxygen, sulfur, SO, SO₂, NH or by —N($C_1$–$C_4$alkyl)—;
$R_{27}$ is hydrogen or $C_1$–$C_4$alkyl;

$R_a$ is hydrogen, halogen, cyano, trifluoromethyl, nitro, $C_1$–$C_4$alkyl, $C_1$–$C_4$alkoxy, $C_1$–$C_4$alkylthio, $C_1$–$C_4$alkylsulfinyl, $C_1$–$C_4$alkylsulfonyl, —COOR$_j$, —CONR$_k$R$_m$, —COR$_n$, —SO₂NR$_k$R$_m$ or —OSO₂—$C_1$–$C_4$alkyl;

$R_g$ is hydrogen, halogen, cyano, nitro, $C_1$–$C_4$alkyl, $C_1$–$C_4$haloalkyl, $C_1$–$C_4$alkylthio, $C_1$–$C_4$alkylsulfinyl, $C_1$–$C_4$alkylsulfonyl, —COOR$_j$, —CONR$_k$R$_m$, —COR$_n$, —SO₂NR$_k$R$_m$, —OSO₂—$C_1$–$C_4$alkyl, $C_1$–$C_6$alkoxy, or $C_1$–$C_6$alkoxy substituted by $C_1$–$C_4$alkoxy or by halogen; $C_3$–$C_6$alkenyloxy, or $C_3$–$C_6$alkenyloxy substituted by halogen; or $C_3$–$C_6$alkynyloxy;

or $R_a$ and $R_b$ together form a $C_3$–$C_4$alkylene bridge that can be substituted by halogen or by $C_1$–$C_4$alkyl, or a $C_3$–$C_4$alkenylene bridge that can be substituted by halogen or by $C_1$–$C_4$alkyl, or a $C_4$alkadienylene bridge that can be substituted by halogen or by $C_1$–$C_4$alkyl;

$R_b$ and $R_h$, independently of one another, are hydrogen, halogen, $C_1$–$C_4$alkyl, trifluoromethyl, $C_1$–$C_6$alkoxy, $C_1$–$C_6$alkylthio or —COOR$_j$;

$R_c$ is hydrogen, halogen, nitro, $C_1$–$C_4$alkyl or methoxy;

$R_d$ is hydrogen, halogen, nitro, $C_1$C$_4$alkyl, $C_1$–$C_4$alkoxy, $C_1$–$C_4$alkylthio, $C_1$–$C_4$alkylsulfinyl, $C_1$–$C_4$alkylsulfonyl, —COOR$_j$ or CONR$_k$R$_m$;

$R_e$ is hydrogen, halogen, $C_1$–$C_4$alkyl, —COOR$_j$, trifluoromethyl or methoxy; or $R_d$ and $R_e$ together form a $C_3$–$C_4$alkylene bridge;

$R_f$ is hydrogen, halogen or $C_1$–$C_4$alkyl;

$R_x$ and $R_y$, independently of one another, are hydrogen, halogen, $C_1$–$C_4$alkyl, $C_1$–$C_4$alkoxy, $C_1$–$C_4$alkylthio, —COOR$_{28}$, trifluoromethyl, nitro or cyano;

$R_j$, $R_k$ and $R_m$, independently of one another, are hydrogen or $C_1$–$C_4$alkyl; or $R_k$ and $R_m$ together form a $C_4$–$C_6$alkylene bridge that can be interrupted by oxygen, NH or by —N($C_1$–$C_4$alkyl)—;

$R_n$ is $C_1$–$C_4$alkyl, phenyl, or phenyl substituted by halogen, $C_1$–$C_4$alkyl, methoxy, nitro or by trifluoromethyl;

$R_{28}$ is hydrogen, $C_1$–$C_{10}$alkyl, $C_1$–$C_4$alkoxy-$C_1$–$C_4$alkyl, $C_1$–$C_4$alkylthio-$C_1$–$C_4$alkyl, di-$C_1$–$C_4$alkylamino-$C_1$–$C_4$alkyl, halo-$C_1$–$C_8$alkyl, $C_2$–$C_8$alkenyl, halo-$C_2$–$C_8$alkenyl, $C_3$–$C_8$alkynyl, $C_3$–$C_7$cycloalkyl, halo-$C_3$–$C_7$cycloalkyl, $C_1$–$C_8$alkylcarbonyl, allylcarbonyl, $C_3$–$C_7$cycloalkylcarbonyl, benzoyl that is unsubstituted or substituted at the phenyl ring by up to three identical or different substituents selected from halogen, $C_1$–$C_4$alkyl, halo-$C_1$–$C_4$alkyl, halo-$C_1$–$C_4$alkoxy and $C_1$–$C_4$alkoxy; or is furoyl or thienyl; or $C_1$–$C_4$alkyl substituted by phenyl, halophenyl, $C_1$–$C_4$alkylphenyl, $C_1$–$C_4$alkoxyphenyl, halo-$C_1$–$C_4$alkylphenyl, halo-$C_1$–$C_4$alkoxyphenyl, $C_1$–$C_6$alkoxycarbonyl, $C_1$–$C_4$alkoxy-$C_1$–$C_8$alkoxycarbonyl, $C_3$–$C_8$alkenyloxycarbonyl, $C_3$–$C_8$alkynyloxycarbonyl, $C_1$–$C_8$alkylthiocarbonyl, $C_3$–$C_8$alkenylthiocarbonyl, $C_3$–$C_8$alkynylthiocarbonyl, carbamoyl, mono-$C_1$–$C_4$alkylaminocarbonyl or by di-$C_1$–$C_4$alkylaminocarbonyl; or phenylaminocarbonyl that is unsubstituted or substituted at the phenyl by up to three identical or different substituents selected from halogen, $C_1$–$C_4$alkyl, halo-$C_1$–$C_4$alkyl, halo-$C_1$–$C_4$alkoxy and $C_1$–$C_4$alkoxy or monosubstituted by cyano or by nitro; or dioxolan-2-yl that is unsubstituted or substituted by one or two $C_1$–$C_4$alkyl radicals; or dioxan-2-yl that is unsubstituted or substituted by one or two $C_1$–$C_4$alkyl radicals; or $C_1$–$C_4$alkyl substituted by cyano, nitro, carboxy or by $C_1$–$C_8$alkylthio-$C_1$–$C_8$alkoxycarbonyl; or of a 1-phenylazole-3-carboxylic acid derivative of formula IIc

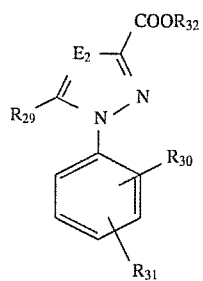

wherein
$E_2$ is nitrogen or methine;
$R_{29}$ is —$CCl_3$, phenyl or halo-substituted phenyl;
$R_{30}$ and $R_{31}$, independently of one another, are hydrogen or halogen; and
$R_{32}$ is $C_1$–$C_4$alkyl;
or of a chloroacetamide of formula IId

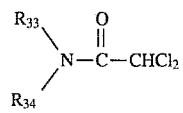

wherein
$R_{33}$ and $R_{34}$, independently of one another, are $C_1$–$C_6$alkyl or $C_2$–$C_6$alkenyl; or $R_{33}$ and $R_{34}$ together are

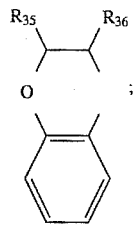

wherein
$R_{35}$ and $R_{36}$, independently of one another, are hydrogen or $C_1$–$C_6$alkyl; or $R_{33}$ and $R_{34}$ together are

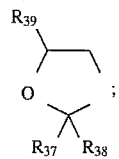

wherein
$R_{37}$ and $R_{38}$, independently of one another, are $C_1$–$C_4$alkyl; or $R_{37}$ and $R_{38}$ together are —$(CH_2)_5$—;
$R_{39}$ is hydrogen, $C_1$–$C_4$alkyl or

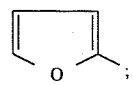

or $R_{33}$ and $R_{34}$ together are or

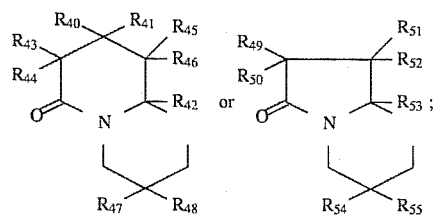

wherein $R_{40}$, $R_{41}$, $R_{42}$, $R_{43}$, $R_{44}$, $R_{45}$, $R_{46}$, $R_{47}$, $R_{48}$, $R_{49}$, $R_{50}$, $R_{51}$, $R_{52}$, $R_{53}$, $R_{54}$ and $R_{55}$, independently of one another, are hydrogen or $C_1$–$C_4$alkyl; or of an oxime of formula IIh

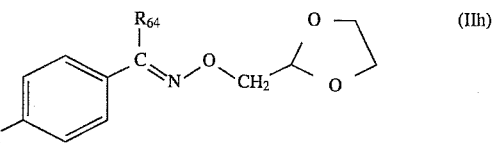

wherein
$R_{63}$ is hydrogen or chlorine and
$R_{64}$ is cyano or trifluoromethyl;
or of a phenylpyrimidine of formula IIi

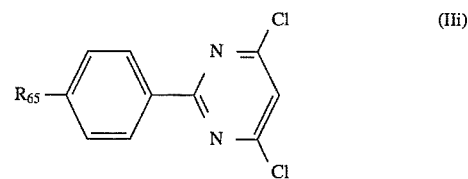

wherein
$R_{65}$ is hydrogen or methyl.

In the definitions used in this description, the generic terms given, as well as the individual definitions of the substituents obtainable by combining individual subsidiary terms, include, for example, the following individual substituents; this list does not represent a limitation of the invention.

In the diagrammatic representation of the substituents $W_1$, $W_2$ and $W_3$ the linkage point to the substituent Y is always at the upper free valency. For example, in the substituent $W_1$ the linkage point to substituent Y is in the ortho-position relative to substituent E.

In the above definitions, halogen is to be understood as being fluorine, chlorine, bromine and iodine, preferably fluorine, chlorine and bromine.

Alkyl is methyl, ethyl, isopropyl, n-propyl, n-butyl, isobutyl, sec-butyl, tert-butyl and the various isomeric pentyl, hexyl, heptyl, octyl, nonyl and decyl radicals.

Haloalkyl is, for example, fluoromethyl, difluoromethyl, trifluoromethyl, chloromethyl, dichloromethyl, trichloromethyl, 2,2,2-trifluoroethyl, 2-fluoroethyl, 2-chloroethyl and 2,2,2-trichloroethyl; preferably trichloromethyl, difluorochloromethyl, trifluoromethyl and dichlorofluoromethyl.

Alkoxy is, for example, methoxy, ethoxy, propoxy, isopropoxy, n-butoxy, isobutoxy, sec-butoxy and tert-butoxy; preferably methoxy and ethoxy. Haloalkoxy is, for example, fluoromethoxy, difluoromethoxy, trifluoromethoxy, 2,2,2-trifluoroethoxy, 1,1,2,2-tetrafluoroethoxy, 2-fluoroethoxy, 2-chloroethoxy and 2,2,2-trichloroethoxy; preferably difluoromethoxy, 2-chloroethoxy and trifluoromethoxy.

Alkylthio is, for example, methylthio, ethylthio, propylthio, isopropylthio, n-butylthio, isobutylthio, sec-butylthio, tert-butylthio or isomeric pentylthio, preferably methylthio and ethylthio.

Alkenyl is to be understood as being straight-chain or branched alkenyl, such as vinyl, allyl, methallyl, 1-methylvinyl, but-2-en-1-yl, pentenyl, 2-hexenyl or 3-heptenyl. Preference is given to alkenyl radicals having a chain length of 2 or 3 carbon atoms.

The alkynyl radicals occurring in the definitions of the substituents may be straight-chain or branched, such as, for example, ethynyl, propargyl, 3-butynyl, 1-methylpropargyl, 1-pentynyl or 2-hexynyl. Ethynyl and propargyl are preferred.

Cycloalkyl is, for example, cyclopropyl, dimethylcyclopropyl, cyclobutyl, cyclopentyl, methylcyclopentyl, cyclohexyl or cycloheptyl, but preferably cyclopropyl, cyclopentyl or cyclohexyl.

Alkoxycarbonyl is, for example: methoxycarbonyl, ethoxycarbonyl, n-propoxycarbonyl, isopropoxycarbonyl and n-butoxycarbonyl, preferably methoxycarbonyl and ethoxycarbonyl.

Alkoxyalkyl is, for example: methoxymethyl, ethoxymethyl, propoxymethyl, methoxyethyl, ethoxyethyl, propoxyethyl, methoxypropyl, ethoxypropyl or propoxypropyl.

Alkylthioalkyl is, for example: methylthiomethyl, ethylthiomethyl, methylthioethyl, ethylthioethyl or isopropylthioethyl.

Alkylaminoalkyl is, for example: methylaminoethyl, dimethylaminoethyl, ethylaminoethyl or diethylaminoethyl.

Cyanoalkyl is, for example: cyanomethyl, cyanoethyl or cyanopropyl.

Halocycloalkyl is, for example: 2,2-dichlorocyclopropyl or pentachlorocyclohexyl.

Alkylsulfonyl is, for example: methylsulfonyl, ethylsulfonyl, propylsulfonyl or butylsulfonyl. Methyl- and ethylsulfonyl are preferred.

Phenyl and thienyl, also as part of a substituent such as phenoxy, thiophenoxy, phenylthio, phenoxycarbonyl, phenylaminocarbonyl, benzyl or benzoyl, can generally be unsubstituted or substituted by further substituents. The substituents may be in the ortho-, meta- and/or para-position(s) or in 2-, 3-, 4- or 5-position of the thienyl ring, respectively. Preferred substituent positions are the ortho- and para-positions to the ring-linkage point. Preferred substituents are halogen atoms.

In the further substituents that are composed of several basic elements, the elements are as defined above by way of example. In those cases also, the lists do not represent a limitation of the invention: they are of an illustrative nature only.

Suitable salts of the free carboxylic acid are, especially, alkali metal salts such as lithium, sodium, potassium; alkaline earth metal salts such as magnesium or calcium; or salts of manganese, copper, zinc or iron; or salts of organic ammonium bases, such as ammonia, primary, secondary or tertiary alkylamines, such as methylammonium, diethylammonium, triethylammonium, morpholinium, tetrabutylammonium, benzyltrimethylammonium, phosphonium, sulfonium, sulfoxonium or pyridinium.

The invention relates also to salts that the compounds of formula I are capable of forming with amines, alkali and alkaline earth metal bases or quaternary ammonium bases. Within the scope of the present invention, those salts also include hydrazonium salts that may be formed by compounds of formula I wherein $R_2$ is the group Q". Salt formation can also be effected by the addition of a strong acid to the pyrimidine moiety of the compounds of formula I. Suitable acids for that purpose are hydrochloric acid, hydrobromic acid, sulfuric acid or nitric acid.

Alkali metal and alkaline earth metal hydroxides that are especially suitable as salt formers are the hydroxides of lithium, sodium, potassium, magnesium or calcium, but especially those of sodium or potassium.

Examples of amines suitable for the formation of ammonium cations are both ammonia and primary, secondary and tertiary $C_1$–$C_4$alkylamines, $C_1$–$C_4$-hydroxyalkylamines and $C_2$–$C_4$alkoxyalkylamines, for example methylamine, ethylamine, n-propylamine, isopropylamine, the four isomeric butylamines, n-amylamine, isoamylamine, hexylamine, heptylamine, octylamine, nonylamine, decylamine, pentadecylamine, hexadecylamine, heptadecylamine, octadecylamine, methyl-ethylamine, methyl-isopropylamine, methylhexylamine, methyl-nonylamine, methyl-pentadecylamine, methyl-octadecylamine, ethyl-butylamine, ethyl-heptylamine, ethyl-octylamine, hexyl-heptylamine, hexyl-octylamine, dimethylamine, diethylamine, di-n-propylamine, diisopropylamine, di-n-butylamine, di-n-amylamine, diisoamylamine, dihexylamine, diheptylamine, dioctylamine, ethanolamine, n-propanolamine, isopropanolamine, N,N-diethanolamine, N-ethylpropanolamine, N-butylethanolamine, allylamine, n-butenyl-2-amine, n-pentenyl-2-amine, 2,3-dimethylbutenyl-2-amine, dibutenyl-2-amine, n-hexenyl-2-amine, propylenediamine, diethanolamine, trimethylamine, triethylamine, tri-n-propylamine, triisopropylamine, tri-n-butylamine, triisobutylamine, tri-sec-butylamine, tri-n-amylamine, methoxyethylamine and ethoxyethylamine; heterocyclic amines, such as pyridine, quinoline, isoquinoline, morpholine, piperidine, pyrrolidine, indoline, quinuclidine and azepine; primary arylamines, such as anilines, methoxyanilines, ethoxyanilines, o,m,p-toluidines, phenylenediamines, benzidines, naphthylamines and o,m,p-chloroanilines; but especially triethylamine, isopropylamine and diisopropylamine.

Examples of quaternary ammonium bases are generally the cations of ammonium halides, for example the tetramethylammonium cation, the trimethylbenzylammonium cation, the triethylbenzylammonium cation, the tetraethylammonium cation, the trimethylethylammonium cation, and also the ammonium cation.

When the substituents $R_a$ and $R_b$ together form a $C_3$–$C_4$alkylene, $C_3$–$C_4$alkenylene or $C_4$alkadienylene bridge, each of which may be substituted by halogen or by $C_1$–$C_4$alkyl, there are formed, together with the phenyl ring to which the bridge is bonded, binuclear systems, such as 1,2,3,4-tetrahydronaphthalene, 1-chloro-2-methyl-3,4-dihydronaphthalene, indanes, 1,2-dihydronaphthalene, indene, naphthalene, 2-methylnaphthalene, 1-n-butylnaphthalene, 2-ethylnaphthalene or 1-chloronaphthalene.

When the substituents $R_d$ and $R_e$ together form a $C_3$–$C_4$alkylene bridge, there are formed, together with the ring system to which they are bonded, polynuclear systems, such as 2,3-tetramethylenethiophene, 2,3-trimethylenethiophene, 2,3-tetramethylenefuran, 3,4-tetramethylenepyridine or

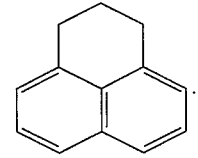

Compounds of formula I, or salts thereof, that are preferred for use in the composition according to the invention are those wherein W is $W_1$, $W_2$, $W_3$ or $W_4$, but especially $W_1$, and wherein Y is preferably —COOH, or an organic or inorganic salt of that acid,

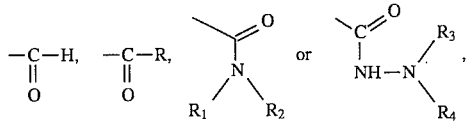

but most especially —COOH, or an organic or inorganic salt of that acid. Of that group, special preference is given to those compounds wherein $R_{12}$ is hydrogen, halogen, —OCH$_3$ or —COR$_{13}$, wherein $R_{13}$ is especially $C_1$–$C_4$alkyl. Preference is also given to those compounds wherein W is $W_1$ and E is nitrogen.

Very especially preferred individual compounds of formula I are listed in the following Tables 1 to 4:

TABLE 1
Compounds of formula Ia
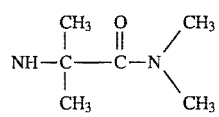
(Ia)
| Comp. No. | X | E | R |
|---|---|---|---|
| 1.001 | S | C—Cl | OH |
| 1.002 | O | CH | OH |
| 1.003 | O | CH | OCH₃ |
| 1.004 | O | N | OC₂H₅ |
| 1.005 | O | C—C(=O)—CH₃ | OCH₃ |
| 1.006 | O | C—F | NH—C(CH₃)₂—C(=O)—N(CH₃)₂ |
| 1.007 | O | C—F | NH—CH(COOC₂H₅)—CH₂CH₂COOC₂H₅ |
| 1.008 | O | CH | NH—N⁺(CH₃)₂·Br⁻ with CH₂COOC₂H₅ |
| 1.009 | O | CH | NH—N(piperidinyl) |
| 1.010 | O | CH | NH—CH(C₂H₅)—C(=O)—NH₂ |
| 1.011 | O | C—F | OH |
| 1.012 | O | C—H | —NH—N(CH₃)₂ |
| 1.013 | O | C—OCH₃ | —NH—NH—(2-Cl-phenyl) |
| 1.014 | O | C—OCH₃ | —NH—NH—(2-F-phenyl) |
| 1.015 | O | C—OCH₃ | —NH—NH—(3-CH₃-phenyl) |

TABLE 1-continued
Compounds of formula Ia
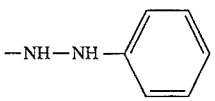
(Ia)
| Comp. No. | X | E | R | |
|---|---|---|---|---|
| 1.016 | O | C—H | —NH—NH— 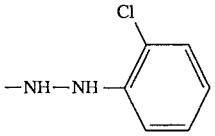 | |
| 1.017 | O | C—H | —NH—NH— 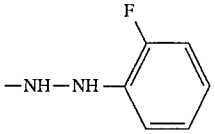 | |
| 1.018 | O | C—H | —NH—NH— 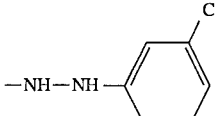 | |
| 1.019 | O | C—H | —NH—NH— 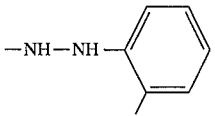 | |
| 1.020 | O | C—H | —NH—NH— 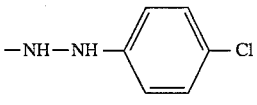 | |
| 1.021 | O | C—H | —NH—NH—  | |
| 1.022 | O | C—H | —NH—NH—C(CH$_3$)$_3$ | |
| 1.023 | O | N | —O— 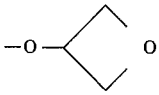 | |
| 1.024 | O | C—F | —O— 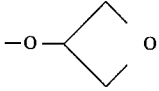 | |
| 1.025 | O | C—H | —O— 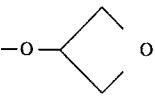 | |
| 1.026 | O | N | —OCH$_2$CH$_2$ON═C(CH$_3$)$_2$ | |
| 1.027 | O | C—OCH$_3$ | OH | |

TABLE 1-continued

Compounds of formula Ia (Ia)

[Structure: benzene ring with E substituent, bearing a C(=O)-R group and an X-linked 4,6-dimethoxypyrimidin-2-yl group]

| Comp. No. | X | E | R |
|---|---|---|---|
| 1.028 | O | [C–O–(4,6-dimethoxypyrimidin-2-yl) group] | OH |
| 1.029 | O | C–F | OH |
| 1.030 | O | C–H | $-NH-N(CH_3)_2$ |

TABLE 2

Compounds of formula Ib (Ib)

[Structure of formula Ib with $R_{22}$, $R_{23}$ substituents, lactone C=O, and X-linked 4,6-dimethoxypyrimidin-2-yl group]

| Comp. No. | X | $R_{23}$ | $R_{22}$ |
|---|---|---|---|
| 2.001 | O | $C_2H_5$ | H |
| 2.002 | S | $CH_3$ | H |
| 2.003 | O | $CH_3$ | H |
| 2.004 | O | $C_2H_5$ | OH |
| 2.005 | S | $CH_3$ | OH |
| 2.006 | S | $C_2H_5$ | H |

TABLE 3

Compounds of formula Ic (Ic)

[Structure of formula Ic with $R_{20}$, $R_{21}$ on C=C, C(=O)-R, and X-linked 4,6-dimethoxypyrimidin-2-yl group]

| Comp. No. | X | R | $R_{21}$ | $R_{20}$ |
|---|---|---|---|---|
| 3.001 | O | OH | $CH_3$ | $CH_3$ |
| 3.002 | O | OH | $C_2H_5$ | $CH_3$ |

TABLE 4

Compounds of formula Id (Id)

[Structure of formula Id with $R_{17}$, $R_{18}$, $R_{19}$ on carbon, C(=O)-R, and X-linked 4,6-dimethoxypyrimidin-2-yl group]

| Comp. No. | X | R | $R_{17}$ | $R_{18}$ | $R_{19}$ |
|---|---|---|---|---|---|
| 4.001 | S | OH | $CH_3$ | $CH_3$ | H |
| 4.002 | O | $NH-CH(CH_3)-COOC_2H_5$ | $CH_3$ | $CH_3$ | H |

TABLE 4-continued

Compounds of formula Id

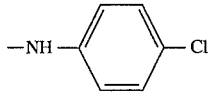

(Id)

| Comp. No. | X | R | $R_{17}$ | $R_{18}$ | $R_{19}$ |
|---|---|---|---|---|---|
| 4.003 | O | NH—CH(COOC$_2$H$_5$)—CH$_2$CH$_2$COOC$_2$H$_5$ | CH$_3$ | CH$_3$ | H |

TABLE 11

Compounds of formula Ie

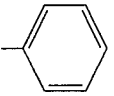

(Ie)

| Comp. No. | X | $R_{66}$ |
|---|---|---|
| 11.01 | O | —NHCH(CH$_3$)$_2$ |
| 11.02 | O | —N(CH$_3$)$_2$ |
| 11.03 | O | —NH—⟨C$_6$H$_4$⟩—Cl |
| 11.04 | O | —OCH$_2$—CH=CH—⟨C$_6$H$_5$⟩ |

In especially preferred compositions according to the invention them are used a herbicidally active pyrimidine of formula I, the above-mentioned preferences being given special mention, and as safener a herbicide-antagonistically effective amount of a quinoline derivative of formula IIg

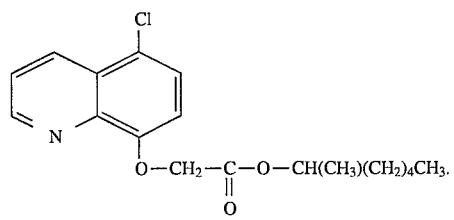

(IIg)

Further safeners of formula IIa that may be given special mention are listed in Table 5:

TABLE 5

Compounds of formula IIa

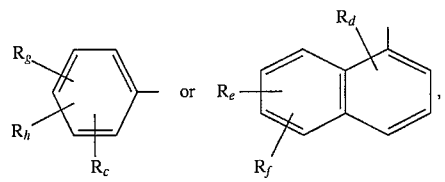

(IIa)

| Comp. No. | $X_2$ | $R_{24}$ |
|---|---|---|
| 5.001 | Cl | CH(CH$_3$)—C$_5$H$_{11}$(n) |
| 5.002 | Cl | C$_4$H$_9$(n) |
| 5.003 | H | H |

Preference is also given to those compositions according to the invention that comprise a herbicide of formula I, special mention being made of the above-mentioned preferred substituents, and a herbicide-antagonistically effective amount of a safener of formula IIb wherein $R_{25}$ is $C_1$–$C_4$alkyl, especially methyl, $R_{26}$ is hydrogen or $C_1$–$C_4$alkyl, $R_{27}$ is hydrogen and $A_2$ is a group $$R_g\text{—}\underset{R_h}{\overset{}{\bigcirc}}\text{—}R_c \quad \text{or} \quad R_e\text{—}\underset{R_f}{\overset{R_d}{\bigcirc\bigcirc}}$$

wherein $R_c$ is preferably hydrogen, $R_g$ is hydrogen, methyl or methoxy, $R_h$ is methyl or methoxy, and $R_d$, $R_e$ and $R_f$ are hydrogen.

Further safeners of formula IIb that may be given special mention are listed as compounds of formula IIe in Table 6:

TABLE 6

Compounds of formula IIe $$A_2\text{—}\overset{O}{\underset{\|}{C}}\text{—NHSO}_2\text{—}\underset{}{\bigcirc}\text{—NH—}\overset{O}{\underset{\|}{C}}\text{—N}\underset{R_{26}}{\overset{CH_3}{\diagup}}$$

(IIe)

| Comp. No. | $A_2$ | $R_{26}$ |
|---|---|---|
| 6.001 | 2-OCH$_3$-phenyl | H |
| 6.002 | 2,4-(CH$_3$)$_2$-phenyl | H |
| 6.003 | 1-naphthyl | CH$_3$ |

TABLE 6-continued

Compounds of formula IIe

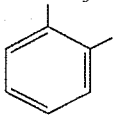

| Comp. No. | A₂ | R₂₆ |
|---|---|---|
| 6.004 | OCH₃ (on tolyl) | CH₃ |

Further preferred compositions according to the invention comprise a herbicide of formula I, special mention being made of the above-mentioned preferred substituents, and a herbicide-antagonistically effective amount of a safener of formula IIc wherein $R_{29}$ is preferably phenyl or halo-substituted phenyl, $R_{30}$ is 2-Cl, $R_{32}$ is methyl and $E_2$ is methine.

Further safeners of formula IIc that may be given special mention are listed as compounds of formula IIf in Table 7:

TABLE 7

Compounds of formula IIf

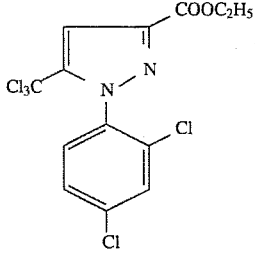

| Comp. No. | R | E₂ | R₃₀ | R₃₁ | R₅₆ |
|---|---|---|---|---|---|
| 7.001 | CH₃ | CH | Cl | H | H |
| 7.002 | CH₃ | CH | Cl | Cl | H |
| 7.003 | CH₃ | CH | F | H | Cl |
| 7.004 | | | | | |

Further preferred compositions according to the invention comprise a herbicide of formula I, the above-mentioned preferred substituents being given special mention, and a herbicide-antagonistically effective amount of a safener of formula IId wherein $R_{33}$ and $R_{34}$ are allyl, or $R_{33}$ and $R_{34}$ together are

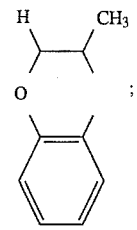

or $R_{33}$ and $R_{34}$ together are

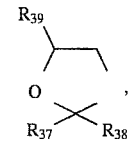

wherein either $R_{37}$ and $R_{38}$ are each methyl and $R_{39}$ is

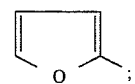

or $R_{37}$, $R_{38}$ and $R_{39}$ are each methyl; or $R_{39}$ is hydrogen; or $R_{37}$ and $R_{38}$ together are —(CH₂)₅—; or $R_{33}$ and $R_{34}$ together are

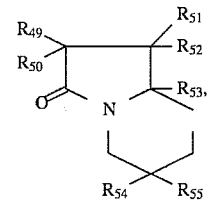

wherein $R_{53}$, $R_{54}$ and $R_{55}$ are preferably methyl and $R_{49}$, $R_{50}$, $R_{51}$ and $R_{52}$ are preferably hydrogen.

Further safeners of formula IId that may be given special mention are listed in Table 8:

TABLE 8

Compounds of formula IId

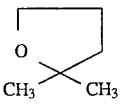

| Comp. No. | $R_{33}$ | $R_{34}$ | $R_{33} + R_{34}$ |
|---|---|---|---|
| 8.001 | $CH_2=CHCH_2$ | $CH_2=CHCH_2$ | — |
| 8.002 | — | — | 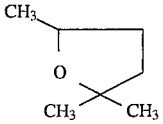 |
| 8.003 | — | — | 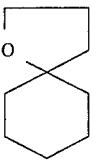 |
| 8.004 | — | — | 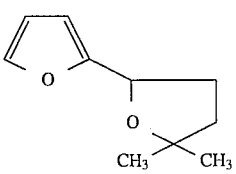 |
| 8.005 | — | — | 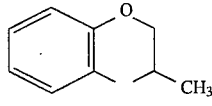 |
| 8.006 | — | — | 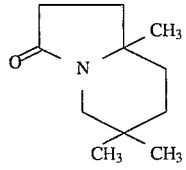 |
| 8.007 | — | — | 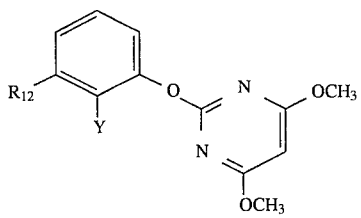 |

Outstanding selective herbicidal compositions according to the invention comprise as herbicide a compound of formula If (If)

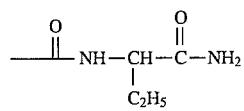

wherein
a) Y is —COOCH₃ and $R_{12}$ is hydrogen; or
b) Y is —COOCH₃ and $R_{12}$ is methylcarbonyl; or
c) Y is —COOCH₃ and $R_{12}$ is ethylcarbonyl; or
d) Y is —COOH and $R_{12}$ is hydrogen; or
e) Y is —COOH and $R_{12}$ is fluorine; or
f) Y is —COOH and $R_{12}$ is methoxy; or
g) Y is 2-chlorophenylhydrazinoyl and $R_{12}$ is methoxy; or
h) Y is 2-fluorophenylhydrazinoyl and $R_{12}$ is methoxy; or
i) Y is o-tolylhydrazinoyl and $R_{12}$ is methoxy; or
j) Y is —NHNHC(CH₃)₃ and $R_{12}$ is hydrogen; or
k) Y is 2-phenylhydrazinoyl and $R_{12}$ is hydrogen; or
Y is 2-fluorophenylhydrazinoyl and $R_{12}$ is hydrogen;
m) Y is 2-trifluoromethylphenylhydrazinoyl and $R_{12}$ is hydrogen; or
n) Y is o-tolylhydrazinoyl and $R_{12}$ is hydrogen; or
o) Y is 4-chlorophenylhydrazinoyl and $R_{12}$ is hydrogen;
p) Y is $$-NH-CH-C-NH_2$$
with $C_2H_5$ side chain and carbonyls and $R_{12}$ is hydrogen; or q) Y is

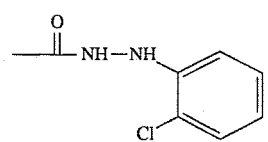

and $R_{12}$ is hydrogen; or r) Y and $R_{12}$ together are

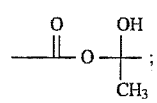

or s) Y and $R_{12}$ together are

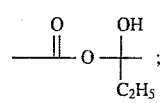

or t) Y and $R_{12}$ together are

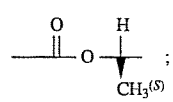

or u) Y and $R_{12}$ together are

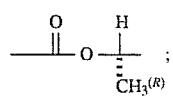

or v) Y and $R_{12}$ together are

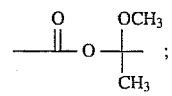

or w) a compound of formula Ig

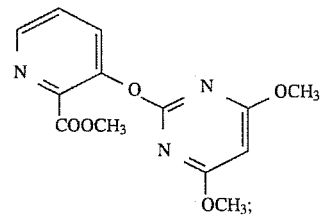

and as safener a herbicide-antagonistically effective amount of a compound of formula IIe

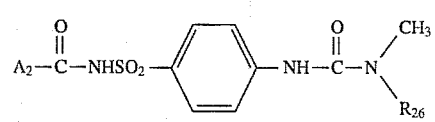

wherein $A_2$ is the group

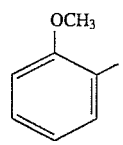

and $R_{26}$ is hydrogen; or of a compound of formula IIe

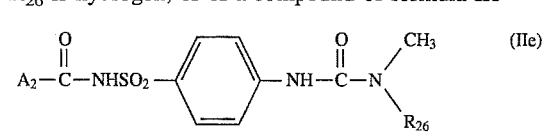 (IIe)

wherein $A_2$ is the group

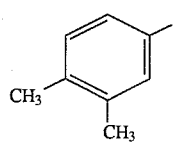

and $R_{26}$ is hydrogen; or of a compound of formula IIe

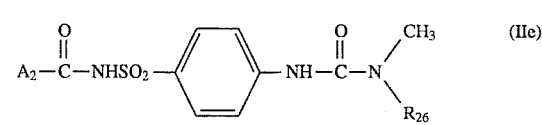 (IIe)

wherein $A_2$ is the group

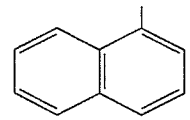

and $R_{26}$ is methyl; or of a compound of formula IIe

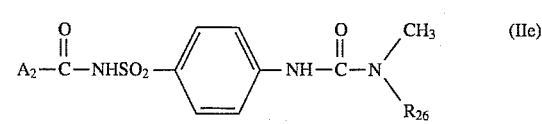 (IIe)

wherein $A_2$ is the group

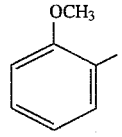

and $R_{26}$ is methyl.

Of that group of compositions according to the invention, special preference is made of those that comprise as herbicide a compound of formula If wherein a) Y is —COOCH$_3$ and $R_{12}$ is hydrogen; or
b) Y is —COOCH$_3$ and $R_{12}$ is ethylcarbonyl; or
c) Y is —COOH and $R_{12}$ is hydrogen; or
d) Y and $R_n$ together are

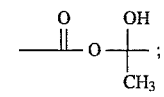

or e) Y and $R_n$ together are

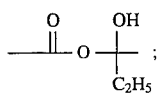

or a compound of formula Ig

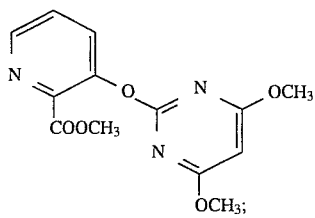
(Ig)

and as safener a herbicide-antagonistically effective amount of a compound of formula IIe

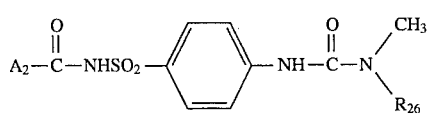
(IIe)

wherein $A_2$ is the group

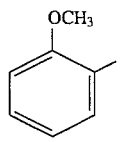

and $R_{26}$ is hydrogen; or of a compound of formula IIe

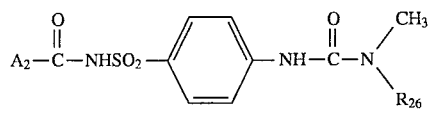
(IIe)

wherein $A_2$ is the group

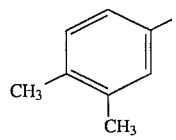

and $R_{26}$ is hydrogen;
or of a compound of IIe

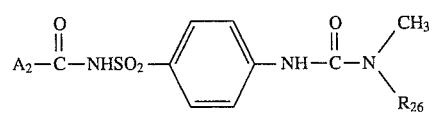
(IIe)

wherein $A_2$ is the group

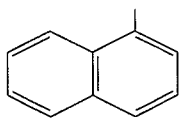

and $R_{26}$ is methyl; or of a compound of formula IIe

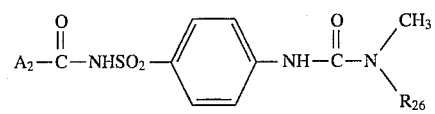
(IIe)

wherein $A_2$ is the group

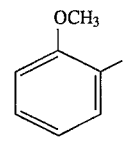

and $R_{26}$ is methyl.

The herbicides of formula I can advantageously also be combined with the safeners mentioned in the following Tables 9 and 10 to form compositions according to the invention:

TABLE 9

Compounds of formula IIh

| Comp. No. | $R_{63}$ | $R_{64}$ |
|---|---|---|
| 9.01 | H | CN |
| 9.02 | Cl | $CF_3$ |

TABLE 10

Compounds of formula IIi

| Comp. No. | $R_{65}$ |
|---|---|
| 10.01 | H |
| 10.02 | $CH_3$ |

Especially outstanding compositions according to the invention comprise the following herbicide/safener combinations:

| Herbicide No. | Safener No. | Herbicide No. | Safener No. |
|---|---|---|---|
| 1.002 + | 5.001 | 1.004 + | 6.001 |
| 1.002 + | 5.004 | 1.004 + | 6.003 |
| 1.002 + | 8.005 | 1.004 + | 6.004 |
| 1.002 + | 9.02 | 1.004 + | 8.07 |
|  |  | 1.004 + | 9.02 |
| 1.011 + | 5.001 | 2.001 + | 6.001 |
| 1.011 + | 5.004 | 2.001 + | 6.003 |
| 1.011 + | 5.005 | 2.001 + | 6.004 |
| 1.011 + | 6.001 |  |  |
| 1.011 + | 6.003 |  |  |
| 1.011 + | 6.004 |  |  |
| 1.011 + | 7.001 |  |  |
| 1.011 + | 8.007 |  |  |
| 2.003 + | 5.001 | 2.004 + | 5.001 |
| 2.003 + | 6.001 |  |  |
| 2.003 + | 6.002 |  |  |
| 2.003 + | 6.004 |  |  |
| 2.003 + | 7.001 |  |  |
| 3.001 + | 5.001 | 3.002 + | 5.001 |
| 3.001 + | 5.004 | 3.002 + | 5.004 |

| Herbicide No. | Safener No. | Herbicide No. | Safener No. |
| --- | --- | --- | --- |
| 3.001 + | 8.005 | 3.002 + | 8.005 |
| 3.001 + | 9.02 | 3.002 + | 9.02 |

The compounds of formulae I, IIa, IIb, IIc, IId, IIh and IIi are known or they can be prepared analogously to known processes. Compounds of formula I are described, for example, in EP-A-0 347 811, 0 335 409, 0426476, 0 315 889, 0435 170, 0402 751, 0 459 243, 0 409 369 and WO 91/05781-A. Compounds of formula I wherein W is $W_5$ or $W_6$ are described in WO 92/17468.

The quinoline derivatives within the scope of formula IIa and their preparation are known or they can be prepared analogously to known processes which are described, for example, in patent specification EP-A-0 094 349. Compounds of formula IIb are described in EP-A-0 365 484 and compounds of formula IIc are described in EP-A-0 268 554 and 0 174 562. Compounds of formula IId are known, for example, from U.S. Pat. No. 4,971,618, U.S. Pat. No. 3,959,304, U.S. Pat. No. 4,256,481, EP-A-0 149 974, EP-A-0 304 409 and DE-OS-2 948 535. Compounds of formula IIh are disclosed in EP-A-0 089 313 and compounds of formula IIi are disclosed in EP-A-0 055 693.

The invention relates also to a method for the selective control of weeds in crops of useful plants, which method comprises treating the useful plants, the seeds or seedlings thereof or the cultivated area thereof with a herbicidally effective amount of the pyrimidine of formula I and a herbicide-antagonistically effective amount of a safener of formula IIa, IIb, IIc, IId, IIh or IIi, simultaneously or independently of one another.

Crop plants that can be protected against the damaging effect of the above-mentioned herbicides by the safeners of formula IIa, IIb, IIc, IId, IIh or IIi are especially those that are important in the food and textile sectors, for example sugar cane and, especially, sorghum, maize, rice and other species of cereal (wheat, rye, barley, oats), most especially wheat and maize.

The weeds to be controlled may be both monocotyledonous and dicotyledonous weeds.

There come into consideration as crop plants or pans of those plants, for example, those mentioned above. Cultivated areas will be understood as meaning areas of land in which the crop plants are already growing or in which the seed of those crop plants has already been sown, and also ground intended for growing those crop plants.

A safener or antidote of formula IIa, IIb, IIc, IId, IIh or IIi can, depending on the intended use, be used to pre-treat the seed of the crop plant (dressing the seeds or seedlings) or can be introduced into the soil before or after sowing has taken place. It can, however, also be applied by itself or together with the herbicide before or after the emergence of the plants. The treatment of the plant or the seed with the safener can therefore in principle take place independently of the time of application of the phytotoxic chemical. The plant can, however, also be treated by applying the phytotoxic chemical and the safener simultaneously (tank mixture). Preemergence treatment includes both treatment of the cultivated area before sowing and treatment of cultivated areas in which seed has been sown but in which the plants have not yet grown.

The rate of application of the safener relative to that of the herbicide depends largely on the mode of application. In the case of field treatment, which is effected either using a tank mixture with a combination of safener and herbicide or by separate application of safener and herbicide, the ratio of safener to herbicide is generally from 1:100 to 10:1, preferably from 1:20 to 1:1, and especially 1:1. In contrast, in the case of seed dressing, much lower amounts of safener are required relative to the rate of application of herbicide per hectare of cultivated area.

In the case of field treatment, 0.001 to 5.0 kg of safener/ha, preferably 0.01 to 0.5 kg of safener/ha, will usually be applied.

The rate of application of herbicide is generally from 0.001 to 2 kg/ha, but preferably from 0.05 to 1 kg/ha.

In the case of seed-dressing, 0.001 to 10 g of safener/kg of seed, preferably 0.05 to 2 g of safener/kg of seed, will generally be applied. If the safener is applied in liquid form by seed soaking shortly before sowing, then it is advantageous to use safener solutions that comprise the active ingredient in a concentration of 1 to 10 000 ppm, preferably 100 to 1000 ppm.

For the purpose of application, the compounds of formula II or combinations of compounds of formula IIa, IIb, IIc, IId, IIh or IIi with the herbicides of formula I to be antagonised are advantageously used together with the adjuvants conventionally employed in formulation technology, and are therefore formulated in known manner, e.g. into emulsifiable concentrates, coatable pastes, directly sprayable or dilutable solutions, dilute emulsions, wettable powders, soluble powders, dusts, granules, and also encapsulations in e.g. polymer substances. As with the nature of the compositions to be used, the methods of application, such as spraying, atomising, dusting, scattering, coating or pouting, are chosen in accordance with the intended objectives and the prevailing circumstances.

The formulations, i.e. the compositions, preparations or mixtures comprising the compound (active ingredient) of formula II, or a combination of the compound of formula IIa, IIb, IIc, IId, IIh or IIi with the herbicide of formula I to be antagonised, and, where appropriate, a solid or liquid adjuvant, are prepared in known manner, e.g. by homogeneously mixing and/or grinding the active ingredients with extenders, e.g. solvents, solid carriers and, where appropriate, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol, ethylene glycol monomethyl or monoethyl ether, ketones such as cyclohexanone, strongly polar solvents such as N-methyl-2-pyrrolidone, dimethyl sulfoxide or dimethylformamide, as well as vegetable oils or epoxidised vegetable oils, such as epoxidised coconut oil or soybean oil; or water.

The solid carriers used e.g. for dusts and dispersible powders are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable nonsorbent carriers are, for example, calcite or sand. In addition, a great number of pregranulated materials of inorganic or organic nature can be used, e.g. especially dolomite or pulverised plant residues.

Depending on the nature of the compound of formula IIa, IIb, IIe, IId, IIh or IIi to be formulated and, where appropriate, also on the nature of the herbicide of formula I to be antagonised, suitable surface-active compounds are non-ionic, cationic and/or anionic surfactants having good emulsifying, dispersing and wetting properties. The term "surfactants" will also be understood as comprising mixtures of surfactants.

Both so-called water-soluble soaps and water-soluble synthetic surface-active compounds are suitable anionic surfactants.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid or of natural fatty acid mixtures which can be obtained e.g. from coconut oil or tallow oil. Fatty acid methyltaurin salts may also be mentioned.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammonium salts and contain a $C_8$–$C_{22}$alkyl radical which also includes the alkyl moiety of acyl radicals, e.g. the sodium or calcium salt of lignosulfonic acid, of dodecylsulfate or of a mixture of fatty alcohol sulfates obtained from natural fatty acids. These compounds also comprise the salts of sulfated and sulfonated fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutylnaphthalenesulfonic acid, or of a condensate of naphthalenesulfonic acid and formaldehyde.

Also suitable are corresponding phosphates, e.g. salts of the phosphoric acid ester of an adduct of p-nonylphenol with 4 to 14 moles of ethylene oxide, or phospholipids.

Non-ionic surfactants are preferably polyglycol ether derivatives of aliphatic or cycloaliphatic alcohols, saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediaminopolypropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, polypropylene/polyethylene oxide adducts, tributylphenoxypolyethoxyethanol, polyethylene glycol and octylphenoxy-polyethoxyethanol.

Fatty acid esters of polyoxyethylene sorbitan, e.g. polyoxyethylene sorbitan trioleate, are also suitable.

Cationic surfactants are preferably quaternary ammonium salts which contain, as N-substituent, at least one $C_8$–$C_{22}$alkyl radical and, as further substituents, unsubstituted or halogenated lower alkyl, benzyl or hydroxy-lower alkyl radicals. The salts are preferably in the form of halides, methyl sulfates or ethyl sulfates, e.g. stearyltrimethyl-ammonium chloride or benzyldi(2-chloroethyl)ethylammonium bromide.

The surfactants customarily employed in formulation technology are described inter alia in the following publications:

"Mc Cutcheon's Detergents and Emulsifiers Annual" MC Publishing Corp., Ridgewood, N.J., 1981.

Stache, H., "Tensid-Taschenbuch", Carl Hanser Verlag, Munich/Vienna 1981.

The agrochemical compositions usually comprise 0.1 to 99% by weight, preferably 0.1 to 95 % by weight, of a compound of formula IIa, IIb, IIc, IId, IIh or IIi or a mixture of antidote and herbicide, 1 to 99.9% by weight, preferably 5 to 99.8% by weight, of a solid or liquid adjuvant and 0 to 25% by weight, preferably 0.1 to 25% by weight, of a surfactant.

Whereas commercial products are preferably formulated as concentrates, the end user will normally employ dilute formulations.

The compositions may also comprise further ingredients such as stabilisers, antifoams, viscosity regulators, binders and tackifiers, as well as fertilisers or other active ingredients for obtaining special effects.

Various methods and techniques are suitable for using compounds of formula IIa, IIb, IIc, IId, IIh or IIi or compositions comprising them for protecting crop plants against the damaging effects of herbicides of formula I. The following are examples thereof:

i) Seed dressing a) Dressing the seeds with a wettable powder formulation of a compound of formula IIa, IIb, IIc, IId, IIh or IIi by shaking in a vessel until the formulation is evenly distributed over the surface of the seeds (dry dressing). Approximately 1 to 500 g of a compound of formula IIa, IIb, IIc, IId, IIh or IIi (4 g to 2 kg of wettable powder) are used per 100 kg of seed.

b) Dressing the seeds with an emulsifiable concentrate of a compound of formula IIa, IIb, IIc, lid, IIh or IIi according to method a) (wet dressing).

c) Dressing by immersing the seeds in a mixture comprising 100 to 1000 ppm of a compound of formula IIa, IIb, IIc, IId, IIh or IIi for 1 to 72 hours and, if desired, subsequently drying the seeds (immersion dressing).

Dressing the seed or treating the germinated seedling are naturally the preferred methods of application since the active ingredient treatment is directed wholly at the target crop. Normally 1 to 1000 g of antidote, preferably 5 to 250 g of antidote, are used per 100 kg of seed, although, depending on the method employed, which also allows the addition of other active ingredients or micronutrients, amounts that exceed or fall short of specified concentration limits may be employed (repeat dressing).

ii) Application from a tank mixture

A liquid formulation of a mixture of antidote and herbicide (ratio of the one to the other from 10:1 to 1:100) is used, the rate of application of herbicide being 0.01 to 5.0 kg per hectare. A tank mixture of this type is applied before or after sowing.

iii) Application to the seed furrow

The antidote is introduced in the form of an emulsifiable concentrate, wettable powder or granules into the open, sown seed furrow and then, after covering the seed furrow, the herbicide is applied preemergence in the normal manner.

iv) Controlled release of active ingredient

A solution of a compound of formula IIa, IIb, IIc, IId, IIh or IIi is applied to mineral granule carriers or polymerised granules (urea/formaldehyde) and allowed to dry. If desired, a coating may be applied (coated granules) that allows the active ingredient to be released in metered amounts over a specific period of time.

Formulation Examples for liquid active ingredients of formula IIa, IIb, IIc, IId, IIh or IIi or mixtures thereof with a herbicide of formula I (throughout, percentages are by weight)

| 1. Emulsifiable concentrates | a) | b) | c) |
|---|---|---|---|
| compound mixture | 25% | 40% | 50% |
| calcium dodecylbenzenesulfonate | 5% | 8% | 6% |
| castor oil polyethylene glycol ether (36 moles of ethylene oxide) | 5% | — | — |
| tributylphenol polyethylene glycol ether (30 moles of ethylene oxide) | — | 12% | 4% |
| cyclohexanone | — | 15% | 20% |
| xylene mixture | 65% | 25% | 20% |

Emulsions of any desired concentration can be produced from such concentrates by dilution with water.

| 2. Solutions | a) | b) | c) | d) |
|---|---|---|---|---|
| compound mixture | 80% | 10% | 5% | 95% |
| ethylene glycol monomethyl ether | 20% | — | — | — |
| polyethylene glycol (mol. wt. 400) | — | 70% | — | — |
| N-methyl-2-pyrrolidone | — | 20% | — | — |
| epoxidised coconut oil | — | — | 1% | 5% |
| petroleum fraction (boiling range 160–190°) | — | — | 94% | — |

These solutions are suitable for application in the form of micro-drops.

| 3. Granules | a) | b) |
|---|---|---|
| compound mixture | 5% | 10% |
| kaolin | 94% | — |
| highly dispersed silicic acid | 1% | — |
| attapulgite | — | 90% |

Ready-for-use dusts are obtained by intimately mixing the carriers with the active ingredient.
The active ingredient is dissolved in methylene chloride, the solution is sprayed onto the carrier, and the solvent is subsequently evaporated off *in vacuo*.

| 4. Dusts | a) | b) |
|---|---|---|
| compound mixture | 2% | 5% |
| highly dispersed silicic acid | 1% | 5% |
| talcum | 97% | — |
| kaolin | — | 90% |

Ready-for-use dusts are obtained by intimately mixing the carriers with the active ingredient.

Formulation Examples for solid active ingredients of formula IIa, IIb, IIc, IId, IIh or IIi or mixtures thereof with a herbicide of formula I (throughout, percentages are by weight)

| 5. Wettable powders | a) | b) | c) |
|---|---|---|---|
| compound mixture | 25% | 50% | 75% |
| sodium lignosulfonate | 5% | 5% | — |
| sodium laurylsulfate | 3% | — | 5% |
| sodium diisobutylnaphthalenesulfonate | — | 6% | 10% |
| octylphenol polyethylene glycol ether (7–8 moles of ethylene oxide) | — | 2% | — |
| highly dispersed silicic acid | 5% | 10% | 10% |
| kaolin | 62% | 27% | — |

The active ingredient is thoroughly mixed with the adjuvants and the mixture is thoroughly ground in a suitable mill, affording wettable powders which can be diluted with water to give suspensions of the desired concentration.

| 6. Emulsifiable concentrates | |
|---|---|
| compound mixture | 10% |
| octylphenol polyethylene glycol ether (4–5 moles of ethylene oxide) | 3% |
| calcium dodecylbenzenesulfonate | 3% |
| castor oil polyglycol ether (35 moles of ethylene oxide) | 4% |
| cyclohexanone | 30% |
| xylene mixture | 50% |

Emulsions of any required concentration can be obtained from this concentrate by dilution with water.

| 7. Dusts | a) | b) |
|---|---|---|
| compound mixture | 5% | 8% |
| talcum | 95% | — |
| kaolin | — | 92% |

Ready-for-use dusts are obtained by mixing the active ingredient with the carriers and grinding the mixture in a suitable mill.

| 8. Extruder granules | |
|---|---|
| compound mixture | 10% |
| sodium lignosulfonate | 2% |
| carboxymethylcellulose | 1% |
| kaolin | 87% |

The active ingredient is mixed and ground with the adjuvants, and the mixture is subsequently moistened with water. The mixture is extruded and then dried in a stream of air.

| 9. Coated granules | |
|---|---|
| compound mixture | 3% |
| polyethylene glycol (mol. wt. 200) | 3% |
| kaolin | 94% |

The finely ground active ingredient is uniformly applied, in a mixer, to the kaolin moistened with polyethylene glycol. Non-dusty coated granules are obtained in this manner.

| 10. Suspension concentrates | |
|---|---|
| compound mixture | 40% |
| ethylene glycol | 10% |
| nonylphenol polyethylene glycol ether (15 moles of ethylene oxide) | 6% |
| sodium lignosulfonate | 10% |
| carboxymethylcellulose | 1% |
| 37% aqueous formaldehyde solution | 0.2% |
| silicone oil in the form of a 75% aqueous emulsion | 0.8% |
| water | 32% |

The finely ground active ingredient is intimately mixed with the adjuvants, giving a suspension concentrate from which suspensions of any desired concentration can be obtained by dilution with water.

BIOLOGICAL EXAMPLES

Example B1

Safener action on maize:

Under greenhouse conditions maize is gown in plastics pots to the two-leaf stage. At that stage, herbicide No. 1.004 by itself and the mixtures of the herbicide with the safeners are applied to the test plants. The test compounds are applied in the form of an aqueous suspension in 500 l of water/ha. The rates of application for the herbicide are given in Table B1 and the rate of application of the safener test compounds is 125 g/ha. 18 days after application the test is evaluated according to a scale of percentages. 100% denotes that the test plant has died, 0% denotes no phytotoxic action. The results in Table B1 show that the safener test compounds clearly reduce the damage to maize caused by the herbicide.

TABLE B1

| Safener | phytotoxicity to maize in % concentration of herbicide in g/ha | | | | |
| --- | --- | --- | --- | --- | --- |
| | 500 | 250 | 125 | 60 | 30 |
| — | 85 | 75 | 50 | 30 | 10 |
| 6.001 | 20 | 10 | 5 | 0 | 0 |
| 6.003 | 25 | 15 | 5 | 0 | 0 |
| 6.004 | 30 | 15 | 10 | 5 | 0 |

Example B2

Safener action on maize:

Under greenhouse conditions maize is grown in plastics pots to the two-leaf stage. At that stage, herbicide No. 1.004 by itself and the mixtures of the herbicide with the safeners are applied to the test plants. The test compounds are applied in the form of an aqueous suspension in 500 l of water/ha. The rates of application for the herbicide are given in Table B2 and the rate of application of the safener test compounds is 125 g/ha. 11 days after application the test is evaluated according to a scale of percentages. 100% denotes that the test plant has died, 0% denotes no phytotoxic action. The results in Table B2 show that the safener test compounds clearly reduce the damage to maize caused by the herbicide.

TABLE B2

| Safener | phytotoxicity to maize in % concentration of herbicide in g/ha | |
| --- | --- | --- |
| | 250 | 125 |
| — | 75 | 60 |
| 8.007 | 35 | 25 |
| 9.02 | 45 | 30 |

Example B3

Safener action on maize and wheat:

Under greenhouse conditions, in plastics pots, maize is grown to the two-leaf stage and wheat to the three-leaf stage. At that stage, herbicide No. 1.002 by itself and the mixtures of the herbicide with the safeners are applied to the test plants. The test compounds are applied in the form of an aqueous suspension in 500 l of water/ha. The rates of application for the herbicide are given in Table B3 and the rate of application of the safener test compounds is 125 g/ha. 22 days after application the test is evaluated according to a scale of percentages. 100% denotes that the test plant has died, 0% denotes no phytotoxic action. The results in Table B3 show that the safener test compounds clearly reduce the damage to maize and wheat caused by the herbicide.

TABLE B3

| Safener | phytotoxicity to: | | | | | |
| --- | --- | --- | --- | --- | --- | --- |
| | maize | | | wheat in % | | |
| | concentration of herbicide in g/ha | | | | | |
| | 80 | 40 | 20 | 80 | 40 | 20 |
| — | 98 | 90 | 80 | 98 | 80 | 70 |
| 5.001 | 55 | 40 | 25 | 20 | 15 | 10 |
| 5.004 | 98 | 85 | 80 | 50 | 15 | 0 |
| 8.005 | 65 | 40 | 15 | 85 | 70 | 45 |
| 9.02 | 80 | 75 | 55 | 85 | 65 | 40 |

Example B4

Safener action on maize:

Under greenhouse conditions maize is grown in plastics pots to the two-leaf stage. At that stage, herbicide No. 2.001 by itself and the mixtures of the herbicide with the safeners are applied to the test plants. The test compounds are applied in the form of an aqueous suspension in 500 l of water/ha. The rates of application for the herbicide are given in Table B4 and the rate of application of the safener test compounds is 125 g/ha. 18 days after application the test is evaluated according to a scale of percentages. 100% denotes that the test plant has died, 0% denotes no phytotoxic action. The results in Table B4 show that the safener test compounds clearly reduce the damage to maize caused by the herbicide.

TABLE B4

| Safener | phytotoxicity to maize in % concentration of herbicide in g/ha | | | | |
| --- | --- | --- | --- | --- | --- |
| | 250 | 125 | 60 | 30 | 15 |
| — | 95 | 90 | 85 | 80 | 60 |
| 6.001 | 40 | 30 | 15 | 5 | 0 |
| 6.003 | 70 | 50 | 10 | 5 | 0 |
| 6.004 | 60 | 20 | 10 | 5 | 0 |

Example B5

Safener action on wheat, barley and rice:

Under greenhouse conditions, in plastics pots, wheat, barley and rice are grown to the two-to three-leaf stage. At that stage, herbicide No. 2.003 by itself and the mixtures of the herbicide with the safeners are applied to the test plants. The test compounds are applied in the form of an aqueous suspension in 500 l of water/ha. The rates of application for the herbicide are 30 and 60 g/ha and the rate of application of the safener test compounds is 60 g/ha. Rice is evaluated according to a scale of percentages 15 days after application, wheat and barley 28 days after application. 100% denotes that the test plant has died, 0% denotes no phytotoxic action. The results in Table B5 show that the safener test compounds clearly reduce the damage to wheat, barley and rice caused by the herbicide.

TABLE B5

| Safener | phytotoxicity to: | | |
| --- | --- | --- | --- |
| | wheat | barley | rice in % |
| Herbicide concentration 30 g/ha: | | | |
| — | 85 | 50 | 20 |
| 5.001 | 30 | 20 | 0 |
| 6.001 | — | — | 0 |

TABLE B5-continued

| Safener | phytotoxicity to: | | |
|---|---|---|---|
| | wheat | barley | rice in % |
| 6.002 | — | — | 0 |
| 6.004 | — | — | 5 |
| 7.001 | 25 | 15 | — |
| Herbicide concentration 60 g/ha: | | | |
| — | 98 | 70 | 35 |
| 5.001 | 70 | 45 | 10 |
| 6.001 | — | — | 10 |
| 6.002 | — | — | 10 |
| 6.004 | — | — | 5 |
| 7.001 | 85 | 25 | — |

Example B6

Safener action on maize and wheat:

Under greenhouse conditions, in plastics pots, maize is grown to the two-leaf stage and wheat to the three-leaf stage. At that stage, herbicides Nos. 3.001 and 3.002 by themselves and the mixtures of the herbicide with the safeners are applied to the test plants. The test compounds are applied in the form of an aqueous suspension in 500 l of water/ha. The rates of application for the herbicide are given in Table B6 and the rate of application of the safener test compounds is 125 g/ha. 22 days after application the test is evaluated according to a scale of percentages. 100% denotes that the test plant has died, 0% denotes no phytotoxic action. The results in Table B6 show that the safener test compounds clearly reduce the damage to maize and wheat caused by the herbicide.

TABLE B6

Herbicide No. 3.001:

| Safener | phytotoxicity to: wheat in % concentration of herbicide in g/ha | | | |
|---|---|---|---|---|
| | 1500 | 800 | 400 | 200 |
| — | 85 | 75 | 65 | 40 |
| 5.001 | 15 | 10 | 5 | 5 |
| 5.004 | 20 | 15 | 0 | 0 |
| 8.005 | 80 | 70 | 25 | 10 |
| 9.02 | 75 | 50 | 25 | 5 |

Herbicide No. 3.002:

| Safener | phytotoxicity to: | | | | | | | |
|---|---|---|---|---|---|---|---|---|
| | maize concentration of herbicide in g/ha | | | | wheat in % | | | |
| | 1500 | 800 | 400 | 200 | 1500 | 800 | 400 | 200 |
| — | 98 | 85 | 65 | 30 | 85 | 70 | 55 | 25 |
| 5.001 | 75 | 40 | 20 | 10 | 20 | 5 | 0 | 0 |
| 5.004 | 90 | 75 | 45 | 10 | 20 | 5 | 0 | 0 |
| 8.005 | 60 | 30 | 20 | 0 | 75 | 45 | 30 | 10 |
| 9.02 | 70 | 55 | 35 | 20 | 75 | 55 | 25 | 15 |

Example B7

Safener action on maize and wheat:

Under greenhouse conditions, in plastics pots, maize is grown to the two-leaf stage and wheat to the three-leaf stage. At that stage, herbicide No. 1.011 by itself and the mixtures of the herbicide with the safeners are applied to the test plants. The test compounds are applied in the form of an aqueous suspension in 500 l of water/ha. The rates of application for the herbicide are 30 and 15 g/ha and the rates of application of the safener test compounds are 60 and 125 g/ha. Maize is evaluated according to a scale of percentages 20 days after application and wheat 21 days after application. 100% denotes that the test plant has died, 0% denotes no phytotoxic action. The results in Table B7 show that the safener test compounds clearly reduce the damage to maize and wheat caused by the herbicide.

TABLE B7

| Safener | concentration in g/ha | phytotoxicity to: | |
|---|---|---|---|
| | | maize | wheat in % |
| Herbicide concentration 30 g/ha: | | | |
| — | — | 95 | 98 |
| 5.001 | 60 | — | 45 |
| 5.004 | 125 | — | 35 |
| 5.005 | 125 | — | 45 |
| 6.001 | 60 | 35 | — |
| 6.003 | 60 | 65 | — |
| 6.004 | 60 | 45 | — |
| 7.001 | 60 | 55 | 25 |
| 8.007 | 60 | 50 | — |
| Herbicide concentration 15 g/ha: | | | |
| — | — | 80 | 90 |
| 5.001 | 60 | — | 30 |
| 5.004 | 125 | — | 15 |
| 5.005 | 125 | — | 15 |
| 6.001 | 60 | 30 | — |
| 6.003 | 60 | 40 | — |
| 6.004 | 60 | 40 | — |
| 7.001 | 60 | 40 | 20 |
| 8.007 | 60 | 25 | — |

Example B8

Comparative postemergent tests of the herbicide compound no. 1.004 alone and in combination with the safener compounds no. 6.001, no. 6.003 or no. 6.004 on zea mays (Zea) and on the 6 weeds Triticum aestivum (Trit), Hordeum vulgare (Hord), Sorghum bicolor (Sorg), Echinochloa crusgalli (Echi), Brachiaria plantaginea (Bra) and Eleusine indica (Eleu):

The test plants were raised in a greenhouse in plastic pots containing standard soil and in the 3- to 4-leaf stage were sprayed with an aqueous suspension of the test compounds prepared from a 25% wettable powder formulation, corresponding to the rates of application as mentioned in the Tables B8.1, B8.2 and B8.3 of active ingredient(s)/hectare (500 l of water/ha). The herbicidal test compound no. 1.004 has been applied individually at the rates of application of 250, 125 and 60 g ai/ha as well as in combination with the safener compounds no. 6.001, 6.003 or 6.004 at the rates of application of the 3 safeners of 125, 60 and 30 g ai/ha. The test was evaluated 19 days after treatment and the phytotoxic action is assessed in percentage toxicity. Rating of 100% activity indicates that the test plants are totally withered (total damage), 0% activity indicates no phytotoxic action (as untreated controls).

The results of the tests are shown on the following tables. The accompanying statement points out the most important observation.

TABLE B8.1

Postemergent test (tankmix application): Compound no. 1.004 individually and in combination with the safener compound no. 6.003; rates of application of compound no. 1.004 are 250, 125 and 60 g ai/ha; rates of application of compound no. 6.003 are 125, 60 and 30 g ai/ha:

| Compound no. | [g ai/ha] | Zea | Trit | Hord | Sorg | Echi | Bra | Eleu |
|---|---|---|---|---|---|---|---|---|
| 1.004 | 250 | 80 | 90 | 90 | 95 | 90 | 95 | 95 |
|  | 125 | 50 | 85 | 90 | 90 | 85 | 90 | 95 |
|  | 60 | 25 | 80 | 85 | 80 | 80 | 85 | 90 |
| 1.004 | 250 + 125 | 15 | 90 | 90 | 95 | 85 | 90 | 95 |
| + | 125 + 125 | 5 | 85 | 90 | 85 | 80 | 85 | 90 |
| 6.003 | 60 + 125 | 0 | 80 | 85 | 80 | 70 | 80 | 90 |
|  | 250 + 60 | 20 | 90 | 90 | 95 | 85 | 90 | 95 |
|  | 125 + 60 | 10 | 85 | 90 | 90 | 80 | 90 | 95 |
|  | 60 + 60 | 5 | 80 | 85 | 85 | 70 | 80 | 85 |
|  | 250 + 30 | 30 | 90 | 90 | 95 | 90 | 90 | 95 |
|  | 125 + 30 | 20 | 85 | 90 | 80 | 85 | 90 | 95 |
|  | 60 + 30 | 10 | 80 | 90 | 85 | 75 | 80 | 90 |

TABLE B8.2

Postemergent test (tankmix application): Compound no. 1.004 individually and in combination with the safener compound no. 6.001; rates of application of compound no. 1.004 are 250, 125 and 60 g ai/ha; rates of application of compound no. 6.001 are 125, 60 and 30 g ai/ha:

| Compound no. | [g ai/ha] | Zea | Trit | Hord | Sorg | Echi | Bra | Eleu |
|---|---|---|---|---|---|---|---|---|
| 1.004 | 250 | 80 | 90 | 90 | 95 | 90 | 95 | 95 |
|  | 125 | 50 | 85 | 90 | 90 | 85 | 90 | 95 |
|  | 60 | 25 | 80 | 85 | 80 | 80 | 85 | 90 |
| 1.004 | 250 + 125 | 10 | 90 | 90 | 95 | 90 | 90 | 95 |
| + | 125 + 125 | 5 | 85 | 90 | 85 | 85 | 85 | 90 |
| 6.001 | 60 + 125 | 0 | 80 | 90 | 80 | 75 | 80 | 90 |
|  | 250 + 60 | 15 | 90 | 90 | 95 | 90 | 90 | 95 |
|  | 125 + 60 | 10 | 85 | 90 | 90 | 85 | 90 | 95 |
|  | 60 + 60 | 0 | 80 | 85 | 85 | 85 | 75 | 95 |
|  | 250 + 30 | 15 | 90 | 90 | 95 | 90 | 90 | 95 |
|  | 125 + 30 | 10 | 85 | 90 | 90 | 85 | 85 | 95 |
|  | 60 + 30 | 0 | 80 | 85 | 80 | 70 | 70 | 95 |

TABLE B8.3

Postemergent test (tankmix application): Compound no. 1.004 individually and in combination with the safener compound no. 6.004; rates of application of compound no. 1.004 are 250, 125 and 60 g ai/ha; rates of application of compound no. 6.004 are 125, 60 and 30 g ai/ha:

| Compound no. | [g ai/ha] | Zea | Trit | Hord | Sorg | Echi | Bra | Eleu |
|---|---|---|---|---|---|---|---|---|
| 1.004 | 250 | 80 | 90 | 90 | 95 | 90 | 95 | 95 |
|  | 125 | 50 | 85 | 90 | 90 | 85 | 90 | 95 |
|  | 60 | 25 | 80 | 85 | 80 | 80 | 85 | 90 |
| 1.004 | 250 + 125 | 15 | 90 | 90 | 90 | 85 | 90 | 95 |
| + | 125 + 125 | 10 | 85 | 90 | 85 | 60 | 90 | 95 |
| 6.004 | 60 + 125 | 5 | 80 | 90 | 80 | 30 | 80 | 95 |
|  | 250 + 60 | 15 | 90 | 90 | 90 | 85 | 85 | 95 |
|  | 125 + 60 | 5 | 85 | 90 | 85 | 65 | 80 | 95 |
|  | 60 + 60 | 0 | 75 | 90 | 80 | 40 | 80 | 95 |
|  | 250 + 30 | 15 | 90 | 90 | 90 | 80 | 90 | 95 |
|  | 125 + 30 | 5 | 85 | 85 | 85 | 65 | 80 | 95 |
|  | 60 + 30 | 0 | 80 | 85 | 80 | 40 | 70 | 95 |

The results in Tables B8.1, B8.2 and B8.3 show that the safener test compounds clearly reduce the damage to maize caused by the herbicide, whereas the phytotoxic action of the safening mixtures toward the weeds is retained.

What is claimed is:

1. A composition for the selective control of weeds in a crop of useful plants, which comprises
   a) a herbicidally effective amount of the herbicide 2-ethoxycarbonyl-3-(4,6-dimethoxypyrimidin-2-yl)oxy-pyridine and
   b) a herbicide-antagonistically effective amount of a safener which is selected from the group consisting of 1-[4-(N-2-methoxybenzoylsulfamoyl)-phenyl]-3-methylurea, 1-[4-(N-4,5-dimethylbenzoylsulfamoyl)-phenyl]-3-methylurea, 1-[4-(N-naphthoylsulfamoyl)-phenyl]-3-dimethylurea, and 1-[4-(N-2-methoxybenzoylsulfamoyl)-phenyl]-3-dimethylurea, and an inert carrier.

2. A method for the selective control of weeds and grasses in a crop of useful plants, which comprises treating the crop, the seeds thereof or the cultivated area thereof with an effective amount of the herbicide 2-ethoxycarbonyl-3-(4,6-dimethoxypyrimidin-2-yl)oxy-pyridine and a herbicide-antagonistically effective amount of a safener which is selected from the group consisting of 1-[4-(N- 2-methoxybenzoylsulfamoyl)-phenyl]-3-methylurea, of 1-[4-(N-4,5-dimethylbenzoylsulfamoyl)-phenyl]- 3-methylurea, 1-[4-(N-naphthoylsulfamoyl)-phenyl]-3-dimethylurea, and 1-[4-(N-2-methoxybenzoylsulfamoyl)-phenyl]-3-dimethylurea, simultaneously or independently of one another.

3. A method of claim 2, which comprises treating crop plants or cultivated areas intended for crop plants with 0.05 to 2 kg/ha of the herbicide and an amount of 0.01 to 0.5 kg/ha of the safener.

4. A method of claim 2 wherein the crop of useful plants is maize or a cereal crop.

* * * * *